(12) United States Patent
Kaniga

(10) Patent No.: US 6,537,558 B2
(45) Date of Patent: *Mar. 25, 2003

(54) METHODS OF PRODUCING AND USING VIRULENCE ATTENUATED POXR MUTANT BACTERIA

(75) Inventor: Koné Kaniga, St. Louis, MO (US)

(73) Assignee: Megan Health, Inc., St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/829,402

(22) Filed: Mar. 31, 1997

(65) Prior Publication Data

US 2002/0090376 A1 Jul. 11, 2002

(51) Int. Cl.$^7$ .................... A61K 39/02; A61K 39/108; A61K 39/112; C12N 1/00

(52) U.S. Cl. .................... 424/234.1; 424/235.1; 424/241.1; 424/258.1; 435/243; 435/252.3

(58) Field of Search .................... 424/234.1, 235.1, 424/241.1, 258.1; 532/23.4; 435/172.1, 252.3; 935/1, 4, 11, 12, 33, 38–41, 44, 47

(56) References Cited

U.S. PATENT DOCUMENTS

| 4,190,495 | A | | 2/1980 | Curtiss |
| 4,968,619 | A | | 11/1990 | Curtiss |
| 5,190,931 | A | | 3/1993 | Inouye |
| 5,643,771 | A | * | 7/1997 | Stocker |
| 5,939,075 | A | * | 8/1999 | Houng et al. |

FOREIGN PATENT DOCUMENTS

| EP | 0 381 706 B1 | 4/1995 |
| WO | 95/14091 | 5/1996 |
| WO | 96/40947 | 12/1996 |

OTHER PUBLICATIONS

O Byrne et al (J. of Bacteriology vol. 176, (3) pp. 905–912), Feb. 1994.*
Kita et al (Microbiology & Immunology vol. 27(2) pp. 117–130), 1983.*
Spaete et al (J. of Virology vol. 56(1) pp. 135–143), Oct. 1985.*
Cherepanov et al (Gene vol. 158 pp. 9–14), 1995.*
Dougan et al., "Live Bacterial Vaccines and Their Application as Carriers for Foreign Antigens" in *Vaccine Biotechnology* (Bittle & Murphy, eds.) pp. 271–300, 1989.
Kaniga et al., "Molecular and functional Characterization of Salmonella poxR gene: Effect on Attenuation of Virulence and Protection" *Abs. Gen. Meet. Am. Soc. Microbiol.* 97(4):78 (May 8, 1997).

Kong et al., "Evidence for a new *Escherichia coli* protein resembling a lysyl–tRNA synthetase" *Gene* 108(1):163–164 (1991).

Sory et al., "Expression of the Eukaryotic *Trypanosoma cruzi* CRA Gene in *Yersinia enterocolitica* and Induction of an Immune Response against CRA in Mice" *Infect. Immun.* 60(9):3830–3836 (Sep. 1992).

Rosqvist et al., "Functional conservation of the secretion and translocation machinery for virulence proteins of yersinia, salmonella and shigellae" *EMBO J.* 14(17);4187–4197 (1995).

Altschul, et al., "Basic Local Alignment Search Tool", J. Mol. Biol., 215:403–410 (1990).

Arthur, et al., "Characterization of TN1546, a Tn3–related transposon conferring glycopeptide resistance by synthesis of depsipeptide peptidoglycan precursors in *Enterococcus faecium* BM4147", J. Bacteriol. 175:(1):117–27 (1993).

Baril, et al., "Cloning of dapD, aroD and asd of Leptospira interrogans serovar icterohaemorrhagiae, and nucleotide sequence of the asd gene", J Gen Microbiol, 138(Pt 1):47–53 (1992).

Begg, et al., "A new *Escherichia coli* cell division gene, ftsK", J Bacteriol, 177(21):6211–22 (1995).

(List continued on next page.)

*Primary Examiner*—Mark Navarro
(74) *Attorney, Agent, or Firm*—Thompson Coburn LLP

(57) ABSTRACT

Disclosed are bacteria having virulence attenuated by a mutation to the regulatory gene poxR. Also disclosed is a method of producing bacteria having virulence attenuated by mutating to the regulatory gene poxR. Such bacteria are useful for inducing an immune response in an animal or human against virulent forms of the bacteria with reduced risk of a virulent infection. Such bacteria are also useful to allow use of normally virulent bacteria as research tools with reduced risk of virulent infection. In a preferred embodiment, poxR attenuated bacteria can be used as a vaccine to induce immunoprotection in an animal against virulent forms of the bacteria. The disclosed bacteria can also be used as hosts for the expression of heterologous genes and proteins or to deliver DNA for genetic immunization. Attenuated bacteria with such expression can be used, for example, to deliver and present heterologous antigens to the immune system of an animal. Such presentation on live bacteria can lead to improved stimulation of an immune response by the animal to the antigens. It has been discovered that bacteria harboring a poxR mutation has significantly reduced virulence. Also disclosed is the nucleotide sequence of the poxR gene from *Salmonella typhimurium*, and the amino acid sequence of the encoded protein. The encoded protein has 325 amino acids and has significant sequence similarity to previously uncharacterized open reading frames in *E. coli* and *Haemophilus influenzae*.

22 Claims, 7 Drawing Sheets

OTHER PUBLICATIONS

Figure 1:
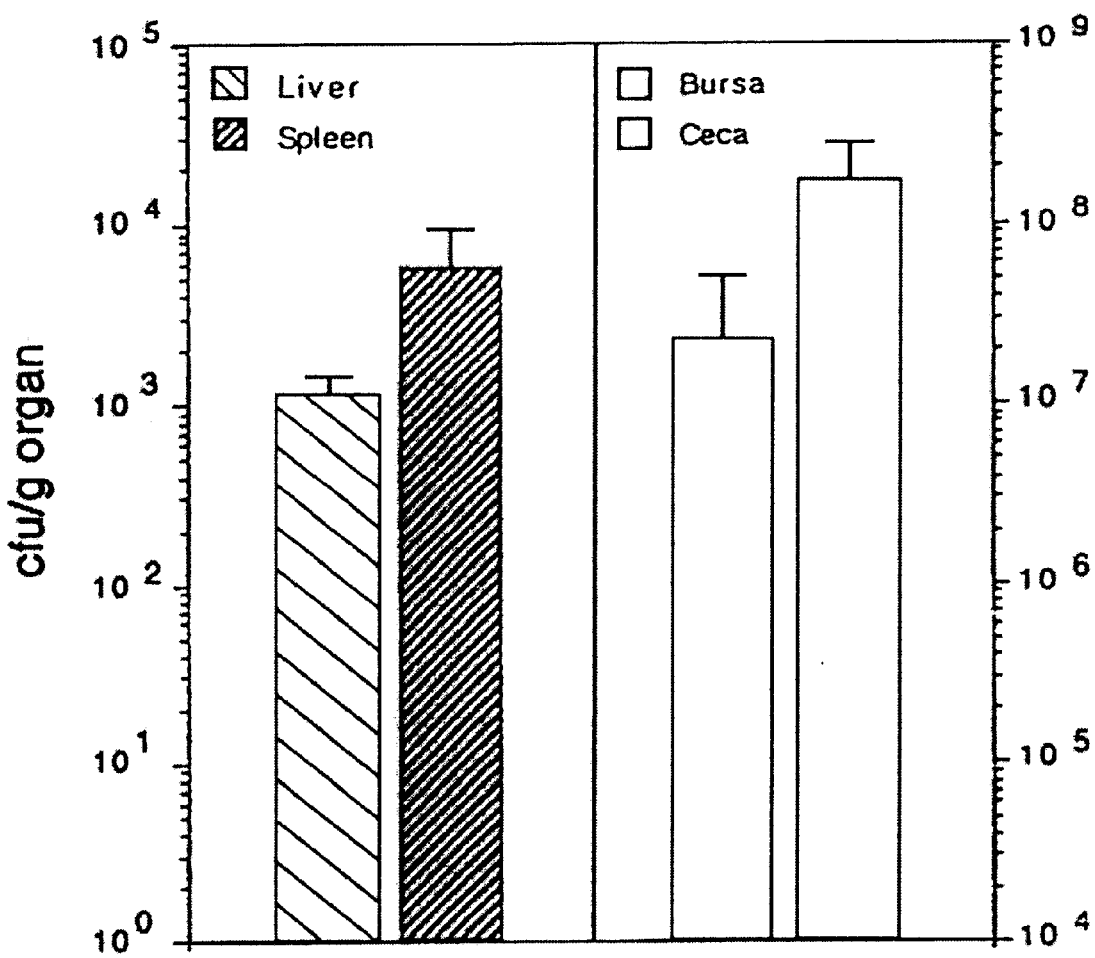

Bertagnolli & Hager, "Role of Flavin in Acetoin Production by Two Bacterial Pyruvate Oxidases", Arch. Biochem. Biophys., 300:364–371 (1993).
*Bertagnolli & Hager, "Activation of *Escherichia coli* Pyruvate Oxidase Enhances the Oxidationof Hydroxyethlthiamin Pyrophosphate", J. Biol. Chem., 266:10168–10173 (1991).
Bienkowska–Szewczyk, et al., The R Gene Product Of Bacteriophase λ, Mol. Gen. Genet., 184:111–114 (1981).
Bochner, et al., "Positive Selection for Loss of Tetracycline Resistance", J. Bacteriol., 143:926 (1980).
Bouloc, et al., "The *Escherichia coli* lov gene product connects peptidoglycan synthesis, ribosomes and growth rate", EMBO 8(1):317–23 (1989).
Bouvier, et al., "Nucleotide sequence and expression of the *Escherichia coli* dapB gene", J Biol Chem. 259(23):14829–34 (1984).
Brosius, "Plasmid Vectors For The Selection Of Promoters", Gene, 27:151–160 (1984).
Brown, et al., "MurA (MurZ), the enzyme that catalyzes the first committed step in peptidoglycan biosynthesis, is essential in *Escherichia coli*", J Bacteriol, 177(14):4194–7 (1995).
Bugg, et al., "Molecular basis for vancomycin resistance in *Enterococcus faecium* BM4147: biosynthesis of a depsipeptide peptidoglycan precursor by vancomycin resistance proteins VanH and VanA", Biochemistry, 30(43):10408–15 (1991).
Buist, et al., "Molecular cloning and nucleotide sequence of the gene encoding the major peptidoglycan hydrolase of *Lactococcus lactis*, a muramidase needed for cell separation", J Bacteriol, 177:(6):1554–63 (1995).
Cádenas & Clements, "Oral Immunization Using Live Attenuated Salmonella spp. as Carriers of Foreign Antigens", Clinical Micro. Rev., 5(3):328–342 (1992).
Cardineau & Curtiss, Nucleotide Sequence Of The asd Gene Of *Streptoccus mutans*, J. Bio. Chem., 262:3344–3353 (1987).
Chakraborti, AS, et al., "Accumulation of a murein–membrane attachment site fraction when cell division is blocked in IkyD and cha mutants of *Salmonella thyphimurium* and *Escherichia coli*", J Bacteriol, 168(3):1422–9 (1986).
Degryse, "Stability of a host–vector system based on complementation of an essential gene in *Escherichia coli*", J Biotechnol, 18:(1–2):29–39 (1991).
Degryse, "Development of stable, genetically well–defined conditionally viable *Escherichia coli* strains", Mol Gen Genet, 227:(1):49–51 (1991).
Deich, et al., "Cloning of genes encoding a 15,000–dalton peptidoglycan–associated outer membrane lipoprotein and an antigenically related 15,000–dalton protein from Haemophilus influenzae", J Bacteriol, 170(2):489–98 (1988).
Doggett & Curtiss, "Delivery Of Antigens By Recombinant Avirulent Salmonella Strains", Adv. Exp. Med. Biol., 327:165–73 (1992).
Doggett, et al., "Immune Responses to SapA–Expressing Recombinant Salmonella," Infect. Immun., 61:1859–1866 (1993).
Dorman, et al., "Characterization Of Porin And ompR Mutants Of A Virulent Strain Of *Salmonella typhimurium:* ompR Mutants Are Attenuated In Vivo", Infect. Immun., 57:2136–40 (1989)

Doublet, et al., "The murI gene of *Escherichi coli* is an essential gene that encodes a glutamate racemase activity", J Bacteriol, 175:(10:2970–9 (1993).
Dougan, et al., "Live Oral Salmonella Vaccines: Potential Use Of Attenuated Strains As Carriers Of Heterologous Antigens To The Immune System", Parasite Immun., 9:151–160 (1987).
Dul, et al., "Genetic Mapping Of A Mutant Defective in D, L–Alanine Racemase in *Bacillus Subtilis* 168", J. Bacteriol., 115:1212 (1973).
Evers, et al., "Sequence of the vanB and ddl genes encoding D–alanine:D–lactate and D–alanine:D–alanine ligases in vancomycin–resistant *Enterococcus faecalis* V583", Gene, 140:(1):97–102 (1994).
Ferrari, et al., "Isolation Of An Alanine Racemase Gene From *Bacillus Subtilis* And Its Use For Plasmid Maintenance in *B. Subtilis*", Bio/Technology, 3:1003–1007 (1985).
Fralick, et al., "Studies on the expression of outer membrane protein 2 in *escherichia coli*", Mol Gen Genet, 188(1):139–42 (1982).
Fugua, et al., "Quorum sensing in bacteria: the LuxR–LuxI family of cell density–responsive transcriptional regulators", J Bacteriol, 176:(2):269–75 (1994).
Galan, et al., "Cloning and characterization of the asd gene of *Salmonella tymphimurium*: use in stable maintenance of recombinant plasmids in Salmonella vaccine strains", Gene, 94(1):29–35 (1990).
Galan & Curtiss, "Virulence ANd Vaccine Potential Of phoP Mutants Of *Salmonella typhimurium*", Microb. Pathogen., 6:433–443 (1989).
Galán, et al., "Molecular and Functional Characterization of the Salmonella Invasion Gene invA: Homology of InvA to Members of a New Protein Family", J. Bacteriol., 17:4338–4349 (1992).
Garrity, et al., "Genetic relationships among actinomycetes that produce the immunosuppressant macrolides FK506, FK520/FK523 and rapamycin", J Ind Microbiol, 12:(1):42–7 (1993).
Gennis & Hager, The enzymes of biological membranes, vol. 2 (Martonosi, ed., New York, N.Y., 1976), pp. 493–504).
Gennis & Stewart, *Escherichia coli* and Salmonella, vol. 1 (Neidhardt, ed., ASM Press, Washinton, D.C., 1996), pp. 217–261.
Gentschev, et al., "Salmonella Strain Secreting Active Listeriolysin Changes Its Intracellular Localization", Infect. Imm., 63(10):4202–4205 (1995).
Gerdes, et al., "Unique Type Of Plasmid Maintenance Function: Postsegregational Killing Of Plasmid–Free Cells", Proc. Natl. Acad. Sci, USA, 83:3116–3120 (1986).
Gerdes et al., "The hok Killer Gene Family In Gram–Negative Bacteria", New Biol., 2:946–956 (1990).
Gerdes, et al., "Mechanism Of Postsegregational Killing By the hok Gene Product Of The parB System Of Plasmid R1 And Its Homology With The re/F Gene Product Of The *E. coli* re/B Operon", EMBO J, 5:2023–2029 (1986).
Germanier & Furer, "Immunity In Experimental Salmonelosis", Infect. Immun., 4:663–73 (1971).
Germanier & Furer, "Isolation And Characterization Of Gal E Mutant Ty 21a Of *Salmonella typhi:* A Candidate Strain For A Live, Oral Typhoid Vaccine", J. Infect. Dis., 131:553–8 (1975).
Giam, et al., "Characterization of a novel lipoprotein mutant in *Escherichia coli*", J Biol Chem, 259:(9):5601–5 (1984).

Giladi, et al., "Integation Host Factor Stimulates The Phage Lambda pL Promoter", J. Mol. Biol., 231:109–121 (1990).

Givskov, et al., "Cloning And Expression In *Escherichia coli* Of The Gene For Extracellular phospholipase A1 From *Serratia liquefaciens*", J. Bacteriol., 170:5855–5862 (1988).

Goodell, et al., "Uptake of cell wall peptides by *Salmonella typhimurium* and *Escherichia coli*", J Bacteriol 169:(8):3861–5 (1987).*

Grabau & Cornan, "In Vivo Function of *Escherichia coli* Pyruvate Oxidase Specifically Requires and Functional Lipid Binding Site", Biochemistry, 25:3748–3751 (1986).*

Gray, et al., "Interchangeabiltiy and Specificity of components from the Quorum–Sensing Regulatory Systems of *Vibrio Fischeri* and *Pseudomonas Aeruginosa*", J. Bacteriology, 176(10):3076–3080 (1994).*

Groisman, et al., "Resistance to Host Antimicrobial Peptides is Necessary for Salmonella Virulence", Proc. Natl. Acad. Sci. USA, 89:11939–11943 (1992).*

Guzman, et al., "Tight Regulation, Modulation, And High–Level Expression by vectors Containing The Arabinose PBAD Promoter", J. Bacteriol., 177(14):4121–4130 (1995).*

Harkness, et al., "In vitro peptidoglycan synthesis by envelopes from *Escherichia coli* tolM mutants is inhibited by colicin M", J Bacteriol., 172:(1):498–500 (1990).*

Hassan, J., et al., "Virulent *Salmonella Typhimurium* Induced Lymphocyte Depletion and Immunosuppression in Chickens," Infect. Immun., 62:2027–2036 (1994).*

Hassan, et al., "Effect of Infective Dose on Humoral Immune Responses and Colonization in Chickens Experimentally Infected with *Salmonella Typhimurium*," Avian Diseases, 37:19–26 (1993).*

Hassan & Curtiss, "Development and Evaluation of an Experimental VaccinationProgram Using a Live Avirulent *Salmonella typhimurium* Strain to Protect Immunized Chickens Against Challenge With Homologous and Heterologous *Salmonella Serotypes*", Infect. Immun., 62(12):5519–5527 (1994).*

Haziza, et al., "Identification of the promoter of the asd gene of *Escherichia coli* using in vitro fusion with the lac operon", Biochimie, 64:(3):227–30 (1982).*

Haziza, et al., "Nucleotide sequence of the asd gene of *Escherichia coli*: absence of a typical attenuation signal", EMBO J, 1(3):379–84 (1982).*

Hecker, et al., "Role Of relA Mutation In The Survival Of Amino Acid–Starved *Escherichia coli*", Arch Microbiol., 143:400–420 (1986).*

Helander, et al., "Preferential Synthesis Of Heptaacyl Lipopolysaccharide By The ssc Permeability Mutant Of *Salmonella typhimurium*", Eur. J. Biochem., 204:1101–1106 (1992).*

Henze, et al., "Influence of femB on methicillin resistance and peptidoglycan metabolism in *Staphylococcus aureus*", J Bacteriol., 175:(6):1612–20 (Mar., 1993).*

Hess, et al., "Superior Efficacy Of Secreted Over Somatic Antigen Display In Recombinant Salmonella Vaccine Induced Protection Against Listeriosis", Proc. Natl. Acad. Sci. USA, 93:1458–1463 (1996).

Hirvas, et al., "Identification And Sequence Analysis Of The Gene Mutated In The Conditionally Lethal Outer Membrane Permeability Mutant SS–C Of *Salmonella typhimurium*", EMBO J., 10(4):1017–1023 (1991).

Ho, et al., "UDP–N–acetylmuramyl–L–alanine functions as an activator in the regulation of the *Escherichia coli* glutamate racemase activity", Biochemistry, 34(8):2464–70 (1995).

Hoe, et al., "Temperature Sensing in *Yersinia pestis:* Regulation Of yopE Transcription By lcrF", J. Bacteriol., 174:4275–4286 (1992).

Hoiseth, et al., "Aromatic–Dependent *Salmonella typhimurium* are Non–Virulent and Effective as Live Vaccines", Nature, 291 (5812):238–239 (1981).

Hone, et al., "A galE via (Vi Antigen–Negative) Mutant Of *Salmonella typhi* Ty2 Retains Virulence In Humans", Infect. Immun. 56:1326–1333 (1988).

Hourdou, et al., "Characterization of the sporulation–related gamma–D–glutamyl–(L)meso–diami-nopimelic–acid–hydrolysing peptidase I of *Bacillus sphaericus* NCT 9602 as a member of the metallo(zinc) carboxypeptidase A family. Modular design of the protein", Biochem J, 292:(Pt 2):563–70 (1993).

Hromockyi, et al., "Temperature Regulation Of Shigella Virulence: Identification Of The Repressor Gene virR, An Analogue Of hns, And Partial Complementation By Tyrosyl Transfer RNA (tRNA1Tyr)", Mol. Micro. 6:2113–2124 (1991).

Jagusztyn–Krynicka, et al., "*E. coli* Heat–Labile Toxin Subunit B Fusions with Streptococcus Sobrinus Antines Expressed by *Solmonella Typhimurium* Oral Vaccine Strains: Importance of the Linker for Antigenicity and Biological Activities of the Hybrid Proteins," Infect. Immun., 61:1004–1015 (1993).

Jagusztyn–Krynicka, et al., "Expression Of Streptococcus mutans Aspartate–Semialdehyde dehydrogenase Gene Cloned Into Plasmid pBR322", J. Gen.Microbiol., 128:1135–1145 (1982).

Johnson, et al., "The Role Of A Stress–Response Protein In *Salmonella typhimurium* Virulence", Mol. Microbiol. 5:401–407 (1991).

Jones, et al., "Induction Of Proteins In Response To Low Temperaure in *Escherichia coli*", J. Bacteriol. 169:2092–2095 (1987).

Kaniga, et al., "The *Salmonella typhimurium* Invasion Genes invF and invG Encode Homologues of the AraC and PulD Family of Proteins", Mol. Microbiol., 13(4):555–568 (1994).

Kaniga, et al., "Identification of Two Targets of the Type III Protein Secretion System Encoded by the inv and spa Loci of *Salmonella typhimurium* That Have Homology to the Sigella IpaD and IpaA Proteins", J. Bacteriol., 177((24):7078–7085 (1995).

Kaniga, et al., "A Wide–Host Suicide Vector For Improving Reverse Genetics In Gram–Negative Bacteria: Inactivation Of The blaA Gene Of *Yersinia enteroclotica*", Gene, 109:137–141 (1991).

Kelly, et al., "Characterization And Protective Properties Of Attenuated Mutants Of *Salmonella choleraesuis*", Infect. Immun. 60:4881–4890 (1992).

Kingsbury, et al., "Temperature–Sensitive Mutants For The Replication of Plasmids In *Escherichia coli:*Requirement For Deoxyribonucleic Acid Polymerase I In The Replication Of The Plasmid ColE1", J. Bacteriol., 114:1116–1124 (1973).

Knudsen & Karlström, "Development of Efficient Suicide Mechanisms for Biological Containment of Bacteria", Applied and Environmental Microbiology, 57(1):85–92 (1991).

Koland, et al., "Reconstitution of the Membrane–Bound, Ubiquinone–Dependent Pyruvate Oxidase Respiratory Chain of *Escherichia coli* with the Cytochrome d Terminal Oxidase", Biochemistry, 23:445–453 (1984).

Kushner, "Construction Of Versatile Low–Copy–Number Vectors For Cloning, Sequencing And Gene Expression In *Escherichia coli*", Gene, 100:195–199 (1990).

Kusser, et al., "Involvement of the relA gene in the autolysis of *Escherichia coli* induced by inhibitors of peptidoglycan biosynthesis", J Bacteriol 164(2):861–5 (1985).

Lambert de Rouvroit, et al., "Role Of The Transcriptional Activator, VirF, And Temperature In The Expression Of The pYV Plasmid Genes Of *Yersinia enterocloitica*", Molec. Microbiol., 6:395–409 (1992).

Latifi, et al., "Multiple homologues of LuxR and Luxl control expression of virulence determinants and secondary metabolites through quorum sensing in *Pseudomonas aeruginosa* PA01", Mol Microbiol, 17:(2):333–43 (1995).

Lennox, "Transduction of Linked Genetic Characters of the Host by Bacteriophage P1", Virology, 1:190–206 (1995)) or Antibiotic No. 2 (Difco, Detroit, Mich.).

Lieb, "Studies Of Heat–Inducible Lambda Bacteriophage", J. Mol. Biol., 16:149–163 (1966).

Lugtenberg, et al., "Temperature–Sensitive Mutant Of *Escherichia coli* K–12 With An Impaired D–Alanine: D–Alanine Ligase", J. Bacteriol., 113:96–104 (1973).

Maidhof, et al., "femA, which encodes a factor essential for expression of methicillin resistance, affects glycine content of peptidoglycan in methicillin–resistant and methicillin–susceptible *Staphylococcus aureus* strains", J Bacteriol, 173:(11):3507–13.

Marsh, et al., "The plC Plasmid and Phage Vectores with Versatile Cloning Sites for Recombinant Selection by Insertional Inactivation", Gene, 32:481–485 (1984).

Maruyama, et al., "Determination of gene products and coding regions from the murE–murF region of *Escherichia coli*", J Bacteriol, 170:(8):3786–8 (1988).

McCarter, "MotY, a component of the sodium–type flagellar motor", J Bacteriol, 176(14):4219–25 (1994).

McEwen, et al., "Synthesis of outer membrane proteins in cpxA cpxB mutants of *Escherichia coli* K–12", J Bacteriol, 154:(1):375–82 (1983).

McGhee & Mestecky, The Secretory Immune System, Ann. N.Y. Acad. Sci., 409 (1983).

Mengin–Lecreuix, et al., "Incorporation of LL–diaminopimelic acid into peptidoglycan of *Escherichia coli* mutants lacking diaminopimelate epimerase encoded by dapF", J Bacteriol, 170:(5):2031–9 (1988).

Mengin–Lecrulx, D, et al., "Identification of the glmU gene encoding N–acetylglucosamine–1–phosphate uridyltransferase in *Escherichia coli*", J Bacteriol 175(19):6150–7 (Oct., 1993).

Michalek, et al., "Antigen Delivery Systems: New Approaches to Mucosal Immunization," *Handbook of Mucosal Immunology*, 373–390 (Academic Press, Inc. 1994).

Miller, et al., "A Two–Component Regulatory System (phoP phoQ) Controls *Salmonella typhimurium* Virulence", Proc. Natl. Acad. Sci. USA, 86:5054–8 (1989).

Miller & Mekalanos, "A Novel Suicide Vector An Its Use In Construction Of Insertion Mutations: Osmoregulation Of Outer Membrane Proteins And Virulence Determinants In *Vibrio choleae* Requires toxR", J. Bacteriol., 170:2575–2583 (1988).

Miyakawa, et al., "Cell Wall Peptidoglycan Mutants Of *Escherichia coli* K–12: Existence Of Two Clusters Of Genes, mra And mrb, For Cell Wall Peptidoglycan Biosynthesis", J. Bacteriol., 112:950 (1972).

Molin, et al., "Conditional suicide system for containment of bacteria and plasmids", Bio/Technology, 5:1315–1318 (1987).

Molin & Kjelleberg, "Releaser of Engineered Microorganisms: Biological Containment and Improved Predictability for Risk Assessment", AMBIO, 22(4):242–245 (1993).

Molin, et al., "Suicidal Genetic Elements And Their Use In Biological Containment Of Bacteria", Annual Review of Microbiology, 47:139–166 (1993).

More, MI, et al., "Enzymatic synthesis of a quorum–sensing autoinducer through use of defined substrates", Science 272:(5268):1655–8 (1996).

Moyed, et al., "hipA, a newly recognized gene of *Escherichia coli* K–12 that affects frequency of persistence after inhibition of murein synthesis", J Bacteriol, 155(2):768–75 (1983).

Munthali, et al., "Restricting the Dispersal of Recombinant DNA: Design of a Contained Biological Catalyst," Bio–Technology, 14(2):189–191 (Feb., 1996).

Munthali, et al., "Use Of Colicin E3 For Biological Containment Of Microorganisms", App. Environ. Microbiol., 62(5):1805–1807 (1996).

Nakayama, et al., "Construction Of An ASD+ Expression–Cloning Vector: Stable Maintenance And High Level Expression Of Cloned Genes In A Salmonella Vaccine Strain", Bio/Technology, 6:693–697 (1988).

Neidhardt, et al., "The Genetics And Regulation Of Heat–Shock Proteins", Annu. Rev. Genet., 18:295–329 (1984).

Nyström, "Role Of Guanosine Tetraphosphate In Gene Expression And The Survival Of Glucose Or Seryl–tRNA Starved Cells Of *Escherichia coli* K12", Mol. Gen. Genet., 245:355–362 (1994).

O'Callaghan & Charbit, "High Efficiency Transformation of *Salmonella typhimurium* and *Salmonella typhi* by Electroporation", Mol. Gen. Genet., 223:157–160 (1990).

O'Connor & Timmis, "Highly Repressible Expression System for Cloning Genes That Specify Potentially Toxic Proteins", J. Bacteriol., 169:4457–4461 (1987).

Peredel'chuck, Miu, et al., "[Cloning the asd and lysC genes from *Cornyebacterium glutamicum*]", *Mol Gen Mikobiol Virusol* (5–6):25–7 (May–Jun., 1992).

Popham, et al., "The *Bacillus subtilis* dacB gene, encoding penicillin–binding protein 5*, is part of a three–gene operon required for proper spore cortex synthesis and spore dehydration", J Bacteriol, 177:(16):4721–9 (1995).

Poteete, et al., "Operator Sequences Of Bacteriophages P22 And 21", J. Mol. Biol., 37:81–91 (1980).

Poulsen, et al., "The gef Gene From *Escherichia coli* Is Regulated At The Level Of Translation", Mol. Microbiol., 5:1639–1648 (1991).

Qoronfleh, et al., "Identification And Characterizaton Of Novel Low–Temperature–Inducible Promoters Of *Escherichia coli*", J. Bacteriol., 174:7902–7909 (1992).

Ramos, et al., "Suicide Microbes on the Loose", Bio/Technology, 13:35–37 (1995).

Reader & Siminovitch, "Lysis Defective Mutants Of Bacteriophage Lambda: On The Role Of The S Function In Lysis[1]", Virology, 43:623–637 (1971).

Reddy, et al., "Hyperexpression And Purification Of *Escherichia Coli* Adenylate Cyclase Using A Vector Designed For Expression Of Lethal Gene Products", Nucleic Acids Res., 17(24):10473–10489 (1989).

Remaut, et al., "Plasmid Vectors For High–Efficiency Expression Controlled By the pL Promoter Of Coliphage Lambda", Gene, 15:81–93 (1981).

Remaut, et al., "Improved Plasmid Vectors With A Thermoinducible Expressiion And Temperature–Regulated Runaway Replication", Gene, 22:103–113 (1983).

Rennell and Poteete, "Phage P22 Lysis Genes: Nucleotide Sequences and Functional Relationships with T4 and λ Genes", Virology, 143:280–289 (1985).

Richaud, C, et al., "Regulation of expression and nucleotide sequence of the *Escherichia coli* dapD gene", *J. Biol Chem* 259:(23):14824–8 (Dec. 10, 1984).

Richaud, et al., "Molecular cloning, characterization, and chromosomal localization of dapF, the *Escherichia coli* gene for diaminopimelate epimerase", *J bacteriol* 169(4):1454–9 (Apr., 1987).

Robbe–Saule, et al., "The Live Oral Typhoid Vaccine ty21a is a rpoS Mutant and is Susceptible to Various Environmental Stresses", FEMS Microbiol. Lett., 126(2):171–176 (1995).

Rodriguez–Herva, et al., "The Pseudomonas putida peptidoglycan–associated outer membrane lipoprotein is involved in maintenance of the integrity of the cell envelope", J Bacteriol, 178(6):1699–706 (1996).

Roten, et al., "Genes involved in meso=diaminopimelate synthesis in *Bacillus subtilis*: Identification of the gene encoding aspartokinase I", J Gen Microbiol, 137:(Pt 4):951–62 (1991).

Rowland, et al., "The *Bacullus subtilis* cell–division 135–137 degrees region contains an essential orf with significant similarity to murB and a dispensable sbp gene", Gene, 164:(1):113–6 (1995).

Russell, et al., "Lipid Activation and Protease Activation of Pyruvate Oxidase", J. Biol. Chem., 252:7883–7887 (1977).

Sahm, et al., "Construction of L–lysine–, L–threonine–, and L–isoleucine– overproducing strains of Croynebacterium glutamicum", Ann N Y Acad Sci, 782:25–39 (1996).

Sanger, et al., "Nucleotide Sequence Of Bacteriophage λ DNA", J. Mol. Biol., 162:729–773 (1982).

Sauer, et al., "Primary Structure Of The Phage P22 Repressor And Its Gene c2", Biochem., 20:3591–3598 (1981).

Schaefer, et al., "Generation of cell–to–cell signals in quorum sensing: acyl homoserine lactone synthease activity of a purified *Vibrio fischeri* Luxl protein", Proc Natl Acad Sci USA, 93:(18):9505–9 (1996).

Schaefer, et al., "Quorum sensing in *Vibrio fischeri:* probing autoinducer–LuxR interactions with autoinducer analogs", J Bacteriol, 178:(10):2897–901 (1996).

*Schmeiger, "Phage P 22–Mutants with Increased of Decreased Transduction Abilities", Mol. Gen. Genet., 119:74–88 (1972).

Schodel, et al., "Development of Recombinant Salmonellae Expressing Hybrid Hepatitis B Virus Core Particles as Candidate Oral Vaccines," Developments in Biological Standardization, 82:151–158 Fred Brown, ed. (Karger 1994).

Schodel, "Hybrid Hepatitis B Virsu core/Pre–S Proteins Synthesized in Avirulent *Salmonella Typhi* for Oral Vaccination," Infect. Immun., 62:1669–1676 (1990).

Schödel, "Recombinant Avirulent Salmonellae as Oral Vaccine Carriers", Infection, 20(1):1–8 (1992).

Schödel, "Oral Vaccination Using Recombinant Bacteria", Semin. Immunol., 2:341–349 (1990).

Schripsema, et al., "Bacteriocin small of *Rhizobium leguminosarum* belongs to the class of N–acly–L–homoserine lactone molecules, known as autoinducers and as quorum sensing co–transcription factors", J Bacteriol, 178:(2):366–71 (Jan., 1996).

Schrock & Gennis, "Specific Ligand Enhancement of the Affinity of *E. Coli* Pyruvate Oxidase for Dipalmitoyl Phosphatidylchline", Biochim. Biophys. Acta, 614:215–220 (1980).

Schweder, et al., "*Escherichia coli* K12 relA strains As Safe Hosts For Expression Of Recombinant DNA", Appl. Microbiol. Biotechnol., 42:718–723 (1995).

Schweder, et al., "An Expression Vector System Providing Plasmid stability and Conditional Suicide of Plasmid–Containing Cells," Appl. Microbiol. Biotechnol., 38:91–93 (1992).

Serebrijski, et al., "Multicopy suppression by asd gene and osmotic stress–dependent complementation by heterologous proA in proA mutants", J Bacteriol, 177:(24):7255–60 (1995).

Sharma, et al., "Expression and characterization of the ponA(ORF I) gene of *Haemophilus influenzae*: functional complementation in a heterologous system", J Bacteriol, 177:(23):6745–60 (Dec., 1995).

Shiumkets, et al., "Induction of coordinated movement of *Myxococcus xanthus* cells", J Bacteriol, 152:(1):451–61 (1982).

Sigwart, et al., "Effect Of A purA Mutation On Efficacy Of Salmonella Live–Vaccine Vectors", Infection and Immunity, 57(6):1858–1861 (1989).

Sizemore, et al., "Attenuated Shigella As A DNA Delivery Vehicle For DNA–Mediated Immunization", Science, 270:299–302 (1995).

Spector & Cubitt, "Starvation–Inducible loci Of *Salmonella thyphiurium*: Regulation And Roles In Starvation: Survival", Mol. Micro., 6:1467–1476 (1992).

Spellerberg, et al., "Pyruvate Oxidase, as a Determinant of Virulence in *Streptococcus Pneumonias*", Molecular Microbiology, 19(4):803–813 (1996).

Stocker, et al., "Aromatic–Dependent <Salmonella Sp.> As Live Vaccine in Mice and Calves", Dev. Biol. Stand., 53:47–54 (1983).

Studier, et al., "Use of T7 RNA Pllymerase to Direct Expression of Cloned Genes", Gene Expression Technology, Methods Enzymol., 185:60–89 (1990).

Studier & Moffat, "Use of Bacteriophage T7 RNA Polymerase to Direct Selective High–Level Expression of Cloned Genes", J. Mol. Biol., 189:113–130 (1986).

Tabor & Richardson, "A Bacteriophage T7 RNA Polymerase/Promoter System for Controlled Exclusive Expression of Specific Genes", Proc. Natl. Acad. Sci. USA, 82:1074–1078 (1985).

Tacket, et al., "Comparison Of The Safety And Immunogenicity Of Δcya Δcrp *Salmonella typhi* Strains In Adult Volunteers", Infect. Immun., 60:536–541 (1992).

Tanabe, et al., "Identification Of The Promoter Region Of The *Escherichia coli* Major Cold Shock Gene, cspA", J. Bacteriol. 174:3867–3873 (1992).

Tao & Blumenthal, "Sequence And Characterization Of pvuIIR, the PvuII Endonculease Gene, And Of puvIIC, Its Regulatory Gene", J. Bacteriol., 174(10):3395–3398 (1992).

Temple, et al., "Survival Of Two Enterobacteria In Feces Buried In Soil Under Field Conditions", Appl. Environ. Microbiol., 40:794–797 (1980).

Tinge & Curtiss, "Conservation of the *Salmonella Typhimurium* Virulence Plasmid Maintenance Regions Among Salmonella Serovars as a Basis for Plasmid Curing," Infect. Immun., 58:3084–3092 (1990).

Tinge & Curtiss, "Isolation of the Replication and Partitioning Regions of the *Salmonella Typhimurium* Virulence Plasmid and Stabilization of Heterologous Replicons," Journal of Bacteriology 172:5266–5277 (1990).

Tobe, et al., "Temperature–Regulated Expression Of Invasion Genes In *Shigella Flexneri* Is Controlled Through The Transcriptional Activation Of The virB Gene On The Large Plamsid", Mol. Micro. 5:887–893 (1991).

Umbarger, "Amino Acid Biosynthesis And Its Regulation", Ann. Rev. Biochem., 47:533 (1978).

Van Dyk, et al., "Pleiotropic Effects of poxA Regulatory Mutations of *Escherichia coli* and *Salmonella Typhimurium*, Mutations Conferring Sufometuron Methyl and α–Ketobutyrate Hypersensitivity", J. Bacteriology, 169(10):4540–4546 (1987).

Van Dyk & LaRossa, "Sensitivity of a *Salmonella Typhimurium* aspC Mutant to Sulfometuron Methyl, a Potent Inhibitor of Acetolactate Synthease II", J. Bacteriol., 165(2):386–392 (1986).

Vasina & Baneyx, "Recombinant Protein Expression At Low Temperatures Under The Transcriptional Control Of The Major *Escherichia coli* Cold Shock Promoter cspA", Appl. Environ. Micro., 62(4):1444–1447 (1996).

Vazquez, et al., "Controlled Expression of Click Beetle Luciferase Using a Bacterial Operator–Repressor System," FEMBs Microbiology Letters, 121:11–18 (1994).

Vuorio & Vaara, "Mutants Carrying Conditionally Lethal Mutations In Outer Membrane Genes omsA And firA (ssc) Are Phenotypically Similar, And omsA Is Allelic To firAp", J. Bacteriol., 174(22):7090–7097 (1992).

Wachi, et al., "Sequence of the downstream flanking region of the shape–determining genes mreBCD of *Escherichia coli*", Gene, 106:(1):135–6 (1991).

Walsh, "Vancomycin resistance: decoding the molecular logic", Science, 261:(5119):308–9 (Jul. 16, 1993).

Walsh, "Enzymes in the D–alanine branch of bacterial cell wall peptidoglycan assembly", J Biol Chem, 264(5):2393–6 (Feb. 15, 1989).

Wijsman, "A Genetic Map Of Several Mutations Affecting The Mucopeptide Layer Of *Secherichia coli*", Genet. Res. Camb., 20:65–74 (1972).

Wijsman, "The Characterization Of An Alanine Racemase Mutant Of *Escherichia coli*", Genet. Res. Camb. 20:269–277 (1972).

Yarrington, et al., "Dual–Origin Plasmid Vectors Whose Origin Of Replication Is Controlled By the Coliphage Lambda Promoters PL", Gene, 28:293–300 (1984).

Yeh, et al., "General organization of the genes specifically involved in the diaminopimelate–lysine biosynthetic pathway of *Corynebacterium glutamicum*", Mol Gen Genet, 212:(1):105–11 (1988).

Young, "Bacteriophage Lysis: Mechanism And Regulation", Microbiol. Rev., 56:430–481 (1992).

Young, et al., "The envA permeability/cell division gene of *Escherichia coli* encodes the second enzyme of lipid A biosynthesis, UDP–3–O–(R–3–hydroxymyristoyl)–N–acetylglucosamine deacetylase", J Biol Chem, 270:(51):30384–91 (1995).

McGovern & Oliver, "Induction of Cold–Responsive Proteins in *Vibrio vulnificus*", J. Bacteriology, 177(14):4131–4133 (1995).

Chang & Cronan, "Genetics and Biochemical Analyses of *Escherichia coli* Strains Having a Mutation in the Structural Gene (poxB) for Pyruvate Oxidase", J. Bacteriol., 154:756–762 (1983).

Chang & Cronan, Jr., "Mapping Nonselectable Genes of *Escherichia coli* by Using Transposon Tn10: Location of a Gene Affecting Pyruvate Oxidase", J. Bacteriology, 151(3):1279–1289 (1982).

Chatfield, et al., "The Development Of Oral Vaccines Based On Live Attenuated Salmonella Strains", FEMS Immunol. Med. Microbiol. 7:1–7 (1993).

Chatfield et al., "Construction Of A Genetically Defined *Salmonella typhi* Mutant For The Engineering Of A Candidate Oral Typhoid–Tetanus Vaccine", Vaccine, 10:53–60 (1992).

Chen, et al., "Organization and nucleotide sequence of the Bacillus subtilis diaminopimelate operon, a cluster of genes encoding the first three enzymes of diaminopimelate synthesis and dipicolinate synthase", J. Biol Chem. 268(13):9448–65 (1993).

Christie, et al., "Synthetic Sites For Transcription Termination And A Functional comparison With Tryptophan Operon Termination Sites In vitro", Proc. Natl. Acad. Sci. USA, 78:4180–4184 (1981).

Cirillo, et al., "Genetic determination of the meso–diaminopimelate biosynthetic pathway of mycobacteria", J. Bacteriol, 176:(14):4424–9 (1994).

Clements, "Use Of Attenuated Mutants Of Salmonella As Carriers For Delivery of Heterologous Antignes To The Secretory Immune System", Pathol. Immunopathol. Res., 6:137–146 (1987).

Collins, et al., "Mutations at rfc or pmi Attenuate Salmonella typhimurium Virulence for Mice", Infect. Immun., 59:1079–1085 (1991).

Collins, et al., "Phylogenetic analysis of a new LL–diaminopimelic acid–containing coryneform bacterium from herbage, Nocardioides plantarum sp. nov.", Int J Syst Bacteriol, 44:(3):523–6 (1994).

Contreras, et al., "Conditional–Suicide Containment System for Bacteria Which Mineralize Aromatics," Applied and Environmental Microbiology, 57(5):1504–1508 (1991).

Curtiss & Tinge, "Recombinant Avirulent Salmonella Vaccines and Prospects for an Antifertility Vaccine," Local Immunicty in Reproductive Tract Tissues, pp. 459–476 (Oxford University Press, Griffin & Johnson, eds., 1993).

Curtiss, et al., "Stabilization of recombinant avirulent vaccine strains in vivo", Res Microbiol, 141(7–8):797–805 (1990).

Curtiss, et al., "Nonrecombinant and Recombinant Avirulent Salmonella Live Vaccines for Poultry," Colonization Control of Human Bacterial Enteropathogens in Poultry, 169–198 (Academic Press, Inc., 1991).

Curtiss, et al., "Chromosomal Aberrations Associated With Mutations To Bacteriophage Resistance In Escherichia Coli", J. Bacteriol., 89:28–40 (1965).

Curtiss, et al., "Live Oral Avirulent Slamonella Vaccines", Veterinary Microbiology, 37:376–405 (1993).

Curtiss, et al., "Nonrecombinant and Recombinant Avirulent Salmonella Vaccines," Recombinant and Synthetic Vaccines, 340–351 (Narosa Publishing House, G.P. Talwar et al. Eds. 1994).

Curtiss, et al., "Avirulent Salmonella Expressing Virulence Antigens From Other Pathogens For Use As Orally Administered Vaccines", Virulence Mechanisms Of Bacterial Pathogens, (Roth, American Society for Microbiology, Washington, D.C., 1988) pp. 311–328.

Curtiss, et al., "Research On Bacterial Conjugation With Mini–Cells And Minicell–Producing E. Coli Strains", Microbial Drug Resistance, 3:169–183 (1982).

Curtiss, "Engineering Organisms For Safety: What is Necessary", The Release Of Genetically–Engineered Micro–Organisms, M. Sussman, et al. editor, Academic Press, 7–20 (1988).

Curtiss, "Genetic Manipulation Of Microorganisms: Potential Benefits And Biohazards", Ann. Rev., 30:507–533 (1976).

Curtiss & Kelly, "Salmonell Typhimurium Deletion Mutants Laking Adenylate Cyclase And Cyclic AMP Receptor Protein Are Avirulent And Immunogenic", Infect. Imm., 55:3035–3043 (1987).

Curtiss, et al., "Recombinant Salmonella Vectors In Vaccine Development", Dev. Biol. Stand., 82:23–33 (1994).

Curtiss, et al., "Selective Delivery of Antigens by Recombinant Bacteria", Curr. Topics Micro. Immun., 146:35–49 (1989).

Curtiss, et al., "Stable Recombinant Avirulent Salmonella Vaccine Strains", Adv. Exp. Med. Biol., 251:33–47 (1989).

Curtiss, "Attenuated Salmonella Strains as Live Vectors for the Expression of Foreign Antigens", New Generation Vaccines (Woodrow and Levine, eds., Marcel Dekker, New York, 1990) pp. 161–188.

Dai, et al., "murH, a new genetic code locus in Escherichia coli involved in cell wall peptidoglycan biosynthesis", J Bacteriol, 170(5):2197–201 (1988).

Dayhoff, et al., "Establishing Homologies inProtein Sequences", Methods in Enzymology, 91:524–545 (1983).

de Jonge, et al., "Altered muropeptide composition in Staphylococcus aureus strains with an inactivated femA locus", J Bacteriol, 175:(9):2779–82 (1993).

* cited by examiner

FIGURE 6A

Sau3AI

GATCGGCTTGAAAGGTTTGCACGACATTCCTCCAGATTATTGTAATTTCACCCTCGCGCAGCCAGATAAAGCCTCTGGGT

TCTGCGAAGTATGAATGCGTTTCCACTGCTCCTTTATGGGTACAACAGTATAGTCTCAGGGATGTGAGGGAAATTTGACG

TGTTCGATTTTTTTAGCGTATCAGAGGGATGAATTATCATTGATTTTGATTAATTTAATTACTAAACCATCTGAAATCAC

TTTTTTTACCCTCCAGAAGGCGCCCGATACGCCTGCGCAAAATTTGTTTCGCCCGCGCGTTGCGAGTAGACTTCGTGACC

```
                         345/1                                              375/11
TTGTCTTAAACTGGAGAAAGAATC ATG AGC GAA ACG GCA ACC TGG CAG CCG AGC GCG TCC ATC CCC
              SD          M   S   E   T   A   T   W   Q   P   S   A   S   I   P

405/21                                      435/31
AAT TTA TTA AAA CGT GCG GCG ATT ATG GCG GAA ATC CGT CGT TTC TTT GGC GAT CGT GGA
 N   L   L   K   R   A   A   I   M   A   E   I   R   R   F   F   G   D   R   G

465/41                                      495/51
GTG CTT GAG GTT GAG ACG CCC TGC ATG AGT CAG GCG ACG GTC ACA GAC ATT CAT CTG TTC
 V   L   E   V   E   T   P   C   M   S   Q   A   T   V   T   D   I   H   L   F

BstBI        525/61                                      555/71
CCG TTC GAA ACG CGT TTC GTC GGA CCT GGC CAT TCC CAG GGG ATC AAC CTC TAT TTA ATG
 P   F   E   T   R   F   V   G   P   G   H   S   Q   G   I   N   L   Y   L   M

585/81                                      615/91
ACC AGT CCG GAA TAC CAT ATG AAA CGC CTG CTG GAG GCA GGG TGC GGC CCG GTT TTC CAG
 T   S   P   E   Y   H   M   K   R   L   L   E   A   G   C   G   P   V   F   Q

645/101                                     675/111
CTA TGC CGC AGT TTC CGT AAT GAA GAG ATG GGA CGA CAT CAT AAT CCG GAA TTC ACT ATG
 L   C   R   S   F   R   N   E   E   M   G   R   H   H   N   P   E   F   T   M

705/121                                     735/131
CTG GAG TGG TAT CGC CCG CAT TAC GAT ATG TAC CGC CTG ATG AAT GAA GTG GAT GAT TTG
 L   E   W   Y   R   P   H   Y   D   M   Y   R   L   M   N   E   V   D   D   L

765/141                                     795/151
CTT CAG CAA GTG CTG GAT TGT CAA CCT GCG GAA AGT CTC TCC TAT CAA CAG GCG TTT CAG
 L   Q   Q   V   L   D   C   Q   P   A   E   S   L   S   Y   Q   Q   A   F   Q

825/161                                     855/171
CGC CAT CTG GGG ATT GAC CCG TTA TCA GCA GAT AAA ACG CAA CTG CGT GAG GCG GCG GCA
 R   H   L   G   I   D   P   L   S   A   D   K   T   Q   L   R   E   A   A   A

825/181                                     915/191
AAG CTT GAT TTA AGC AAT ATC GCC GAT ACG GAA GAA GAC CGT GAT ACG TTG CTG CAA CTG
 K   L   D   L   S   N   I   A   D   T   E   E   D   R   D   T   L   L   Q   L

945/201                                     975/211
TTG TTC ACG ATG GGG GTT GAG CCG CAT ATA GGT AAA GAA AAG CCG ACC TTT ATT TAT CAC
 L   F   T   M   G   V   E   P   H   I   G   K   E   K   P   T   F   I   Y   H

1005/221                                    1035/231
TTT CCG GCA AGT CAG GCA TCG CTG GCA CAA ATC AGT ACC GAG GAT CAT CGC GTC GCC GAG
 F   P   A   S   Q   A   S   L   A   Q   I   S   T   E   D   H   R   V   A   E

1065/241                                    1095/251
CGC TTT GAG GTC TAC TAC AAA GGT ATT GAG CTG GCG AAT GGT TTC CAC GAA CTG ACG GAC
 R   F   E   V   Y   Y   K   G   I   E   L   A   N   G   F   H   E   L   T   D
```

FIGURE 6B

```
                1125/261                                           1155/271
GCA CGT GAG CAA CAA CAG CGC TTT GAA CAG GAC AAT CGT AAG CGC GCC GCT CGC GGT CTG
 A   R   E   Q   Q   Q   R   F   E   Q   D   N   R   K   R   A   A   R   G   L

1185/281                                           1215/291
GCG CAG CAG CCG ATG GAC CAA AAT CTA CTG GAT GCG CTG GCC GCC GGT CTA CCG GAT TGT
 A   Q   Q   P   M   D   Q   N   L   L   D   A   L   A   A   G   L   P   D   C

1245/301                                           1275/311
TCC GGC GTG GCG CTG GGT GTT GAT CGT CTG GTG ATG CTG GCG CTG GGA GCA GAA AGC CTG
 S   G   V   A   L   G   V   D   R   L   V   M   L   A   L   G   A   E   S   L

1305/321
GCG GAC GTG ATT GCT TTT ACG GTC GAT CGG GCG TAA ATCTGAAATTCACTCTTTCGCGAGAGAAAAAT
 A   D   V   I   A   F   T   V   D   R   A   *

GGCGCAATAAGCGCCATTTTGTAGCATATTTTTTCAATTATCCTCTGTTTGGCACAACATAAGGCTGGAACTTTGATGC

CATTTAGGTATCAATCCTGTGTTGATTTTTTTATCGCTGACCTTCGTAAAAAAGAAGGCGGCGTCAATCGGTGAGCGGC

XhoI                    1548/1                                          1578/11
GTCTGGCAAACGCGCTCGAGCGTAAGGGATGGTTGA ATG ACC CAC ACG ATA AAA AAG ATG AGC CTT ATT
                         SD           M   T   H   T   I   K   K   M   S   L   I

1608/21                                            1638/31
GGG CTT ATC CTG ATG ATT TTT ACT TCT GTT TTT GGT TTT GCG AAT AGC CCG TCG GCG TTT
 G   L   I   L   M   I   F   T   S   V   F   G   F   A   N   S   P   S   A   F

1668/41                                            1698/51
TAT TTA ATG GGG TAT AGC GCA ATC CCA TGG TAT ATA TTT TCT GCC TTG CTG TTT TTT ATT
 Y   L   M   G   Y   S   A   I   P   W   Y   I   F   S   A   L   L   F   F   I

1728/61                                            1758/71
CCA TTC GCC TTA ATG ATG GCT GAA ATG GGT TCC GCT TAT CCC AAA GAA GAG GGC GGG ATC
 P   F   A   L   M   M   A   E   M   G   S   A   Y   P   K   E   E   G   G   I

1788/81                                            1818/91
TAT TCG TGG ATG AAT AAT AGC GTG GGG CCA CGT TAC GCG TTT ATT GGC ACG TTT ATG TGG
 Y   S   W   M   N   N   S   V   G   P   R   Y   A   F   I   G   T   F   M   W

1848/101                                           1878/111
TTT TCA TCG TAT GTC ATA TGG ATG GTA AGT ACG GCG GCA AAA ATT TGG GTA CCG TTT TCT
 F   S   S   Y   V   I   W   M   V   S   T   A   A   K   I   W   V   P   F   S

1908/121                                           1938/131
ACA TTT GTT TTT GGC CCC GAT ATG ACG CAG CAC TGG CGT ATT GCA GGG CTT GAG CCT ACG
 T   F   V   F   G   P   D   M   T   Q   H   W   R   I   A   G   L   E   P   T

1968/141                                           1998/151
CAG GTT GTC GGG CTG CTC GCC GTC GGC TGG ATG AAT CTG GTG ACG TGT GTC GCC GCC AGA
 Q   V   V   G   L   L   A   V   A   W   M   N   L   V   T   C   V   A   A   R

BamHI
GGG ATC C
 G   I
```

METHODS OF PRODUCING AND USING VIRULENCE ATTENUATED POXR MUTANT BACTERIA

BACKGROUND OF THE INVENTION

The disclosed invention is in the general areas of bacteria with attenuated virulence and live bacterial vaccines.

The poxA gene (Van Dyk et al., *J. Bacteriology*169(10): 4540–4546 (1987)), is a regulatory gene affecting expression of pyruvate oxidase (Chang and Cronan, *J. Bacteriology* 151(3): 1279–1289 (1982)). The poxA gene of *E. coli* is located at min 94. Enzymological and immunological data indicate that mutations in poxa have an 8 to 10-fold decrease in pyruvate oxidase levels (Chang and Cronan (1982); Chang and Cronan, *J. Bacteriol*. 154:756–762 (1983)). It has also been reported that poxA mutants grow more slowly than the isogenic wild-type in both minimal and rich media, while poxB mutants exhibit normal growth. Van Dyk and LaRossa, *J. Bacteriol*. 165(2):386–392 (1986), isolated 15 mutant *Salmonella typhimurium* strains sensitive to the herbicide sulfometuron methyl (SM) [N-[(4,6-dimethylpyrimidin-2-yl)aminocarbonyl]-2-methoxycarbonyl-benzenesulfonamide], following Tn10 mutagenesis. Among these SM-hypersensitive mutations, a poxA mutation was identified and mapped to the 94 min region of *S. typhimurium* genetic map (Van Dyk et al. (1987)), a location analogous to that of poxA in *E. coli*. The *S. typhimurium* poxA mutant, similarly to the *E. coli* poxA mutant, had reduced pyruvate oxidase activity and reduced growth rates (Van Dyk et al. (1987)). Furthermore, the *E. coli* and *S. typhimurium* poxA mutants shared several additional phenotypes including hypersensitivity to SM, to α-ketobutyrate, and to a wide range of bacterial growth inhibitors, such as antibiotics, amino acid analogs and dyes (Van Dyk et al. (1987)).

The immune system of animals is especially suited to reacting to and eliminating microorganisms which infect the animal. The sustained presence of the full range of antigens expressed by infecting microorganisms provide a stimulating target for the immune system. It is likely that these characteristics lead to the superior efficacy, on average, of vaccines using live attenuated virus. For similar reasons, live bacterial vaccines have been developed that express a desired antigen and colonize the intestinal tract of animals (Curtiss et al., *Curr. Topics Micro. Immun.* 146:35–49 (1989); Curtiss, Attenuated Salmonella Strains as Live Vectors for the Expression of Foreign Antigens, in *New Generation Vaccines* (Woodrow and Levine, eds., Marcel Dekker, New York, 1990) pages 161–188; Schödel, *Infection* 20(1): 1–8 (1992); Cárdenas and Clements, *Clinical Micro. Rev*. 5(3):328–342 (1992)). Most work to date has used avirulent *Salmonella typhimurium*strains synthesizing various foreign antigens for immunization of mice, chickens and pigs. Several avirulent *S. typhi* vectors have been evaluated in human volunteers (Tacket et al., *Infect. Immun.*60:536–541 (1992)) and several phase I clinical trials with recombinant avirulent *S. typhi* strains are in progress in the U.S. and Europe. An important safety advantage of the live attenuated bacterial vaccine vectors as compared to the use of viral vector based vaccines is the ability to treat an immunized patient with oral ciprofloxacin or amoxicillin, should an adverse reaction occur.

It is understood that live bacteria administered to animals, and especially to humans, should not be pathogenic. Thus, live bacterial vaccines need to be avirulent. However, many bacteria that are most effective in stimulating an immune response, and would thus be most attractive as the subject of a live bacterial vaccine, are also the most virulent. Accordingly, there is a need for methods to reduce, or attenuate, the virulence of bacteria.

It is therefore an object of the present invention to provide a method of attenuating the virulence of a bacteria.

It is another object of the present invention to provide a method for inducing an immune response in an animal using bacterial cells with attenuated virulence.

It is another object of the present invention to provide compositions for inducing an immune response in an animal comprising bacterial cells with attenuated virulence.

It is another object of the present invention to provide an isolated nucleic acid molecule containing or encoding the poxR gene.

BRIEF SUMMARY OF THE INVENTION

Disclosed are bacteria having virulence attenuated by a mutation to the regulatory gene poxR. Also disclosed is a method of producing bacteria having virulence attenuated by mutating the regulatory gene poxR. Such bacteria are useful for inducing an immune response in an animal or human against virulent forms of the bacteria with reduced risk of a virulent infection. Such bacteria are also useful to allow use of normally virulent bacteria as research tools with reduced risk of virulent infection. In a preferred embodiment, poxR attenuated bacteria can be used as a vaccine to induce immunoprotection in an animal or human against virulent forms of the bacteria. The disclosed bacteria can also be used as hosts for the expression of heterologous genes and proteins. Attenuated bacteria with such expression can be used, for example, to deliver and present heterologous antigens to the immune system of an animal. Such presentation on live bacteria can lead to improved stimulation of an immune response by the animal to the antigens.

The poxR gene, which is referred to in the literature as poxA (Van Dyk et al., *J. Bacteriology* 169(10):4540–4546 (1987)), is a regulatory gene affecting expression of pyruvate oxidase (Chang and Cronan, *J. Bacteriology*151(3): 1279–1289 (1982)) and having other, pleiotropic effects. The pleiotropic phenotype effects include reduced pyruvate oxidase activity, reduced growth rate, hypersensitivity to the herbicide sulfometuron methyl, to α-ketobutyrate and to amino acid analogs, and failure to grow in the presence of the host antimicrobial peptide, protamine. It has now been discovered that bacterial cell harboring a poxR mutation has significantly reduced virulence. Also disclosed is the nucleotide sequence of the poxR gene from *Salmomella typhimurium*, and the amino acid sequence of the encoded protein. The encoded protein has 325 amino acids and has significant sequence similarity to previously uncharacterized open reading frames in *E. coli* and *Haemophilus influenzae*.

BRIEF DESCRIPTION OF THE DRAWINGS

FIG. 1 is a graph of the number of poxR mutant *S. typhimurium* UK-1 cells colonizing various organs (measured in colony forming units per gram of organ) in day-old chicks. Chicks were orally inoculated with $1\times10^8$ cfu of poxR401::Tn10 strain MGN-791s at day of hatch. All birds survived and six days post-infection, the colonization levels in the spleen, liver, bursa and cecum were determined.

FIG. 2 is a graph of the number of poxR mutant *S. typhimurium* cells colonizing various organs (measured in mean colony forming units per organ) in BALB/c mice.

Each time point consisted of group of three female BALB/c mice six weeks-old. Mice were inoculated orally (p.o.) with $2.6 \times 10^9$ cfu at day 1. Three and seven days post-inoculation, mice were humanely euthanized and spleens (SP), mesenteric lymph nodes (MLN), and Peyer's patches (PP) were removed. The organs were disrupted in one milliliter of buffer saline and 0.1 ml of appropriate dilutions were plated in triplicate on MacConkey lactose plates.

Figure 3C:
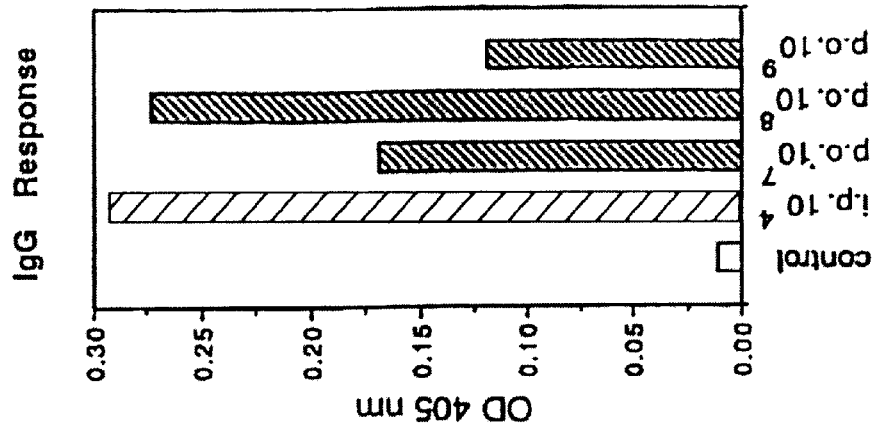
Figure 3B:
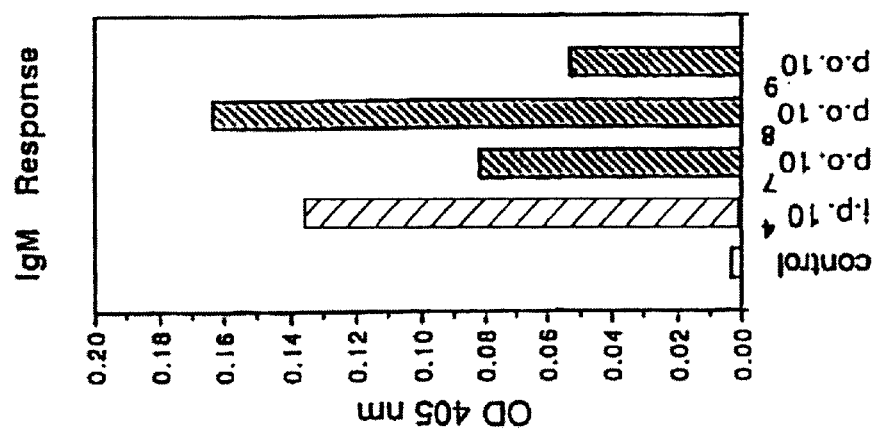
Figure 3A:
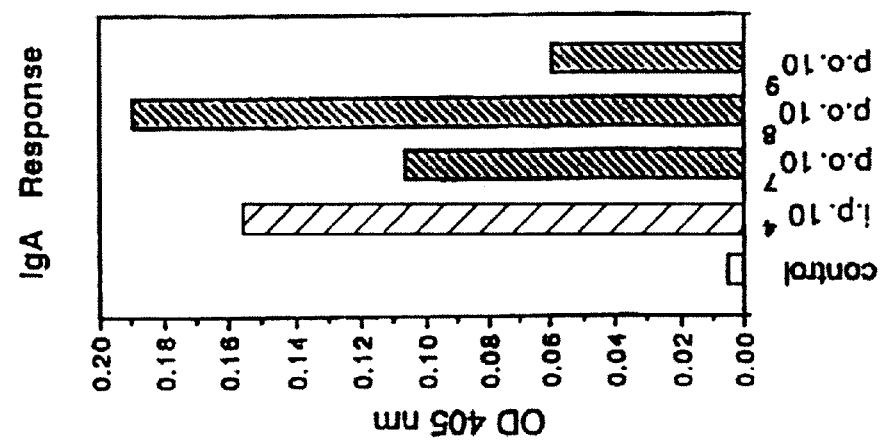

FIGS. 3A, 3B, and 3C are graphs of the immune responses (measured as optical density at 405 nm of ELISA assays) of mice immunized with various amounts of *S. typhimurium* poxR mutant. The optical density at 405 nm in the ELISA assays is a measure of the level of immunoreactive antibodies present. FIG. 3A graphs the IgA response. FIG. 3B graphs the IgM response. FIG. 3C graphs the IgG response. Each treatment group consisted of five female BALB/c mice six weeks-old. Mice were inoculated intra peritoneally (i.p.) with $2.6 \times 10^4$ cfu, and orally (p.o.) with $2.6 \times 10^7$, $2.6 \times 10^8$, and $2.6 \times 10^9$ cfu at day 1. No booster immunization was performed. At day 28 post-immunization, sera were collected from immunized and non immunized control mice and subjected to an ELISA assay using purified Salmonella LPS as coating antigen. The graphs represent the mean absorbance at 405 nm (OD) for five mice. For individual mice, the serum was considered positive when the OD was greater than the mean OD of control mice plus two times the standard deviation of the same control sera. For the IgA response, 5/5 were positive in the i.p. group, 3/5 in the p.o. $2.6 \times 10^7$ cfu group; 5/5 in the p.o. $2.6 \times 10^8$ cfu group; 3/5 in the p.o. $2.6 \times 10^9$ cfu group. For the IgM response, 3/5 were positive in the i.p. group; 2/5 in the p.o. $2.6 \times 10^7$ cfu group; 2/5 in the p.o. $2.6 \times 10^8$ cfu group; 2/5 in the p.o. $2.6 \times 10^9$ cfu group. For the IgG response, 5/5 were positive in the i.p. group; 4/5 in the p.o. $2.6 \times 10^7$ cfu group; 5/5 in the p.o. $2.6 \times 10^8$ cfu group; 3/5 in the p.o. $2.6 \times 10^9$ cfu group.

Figure 4:
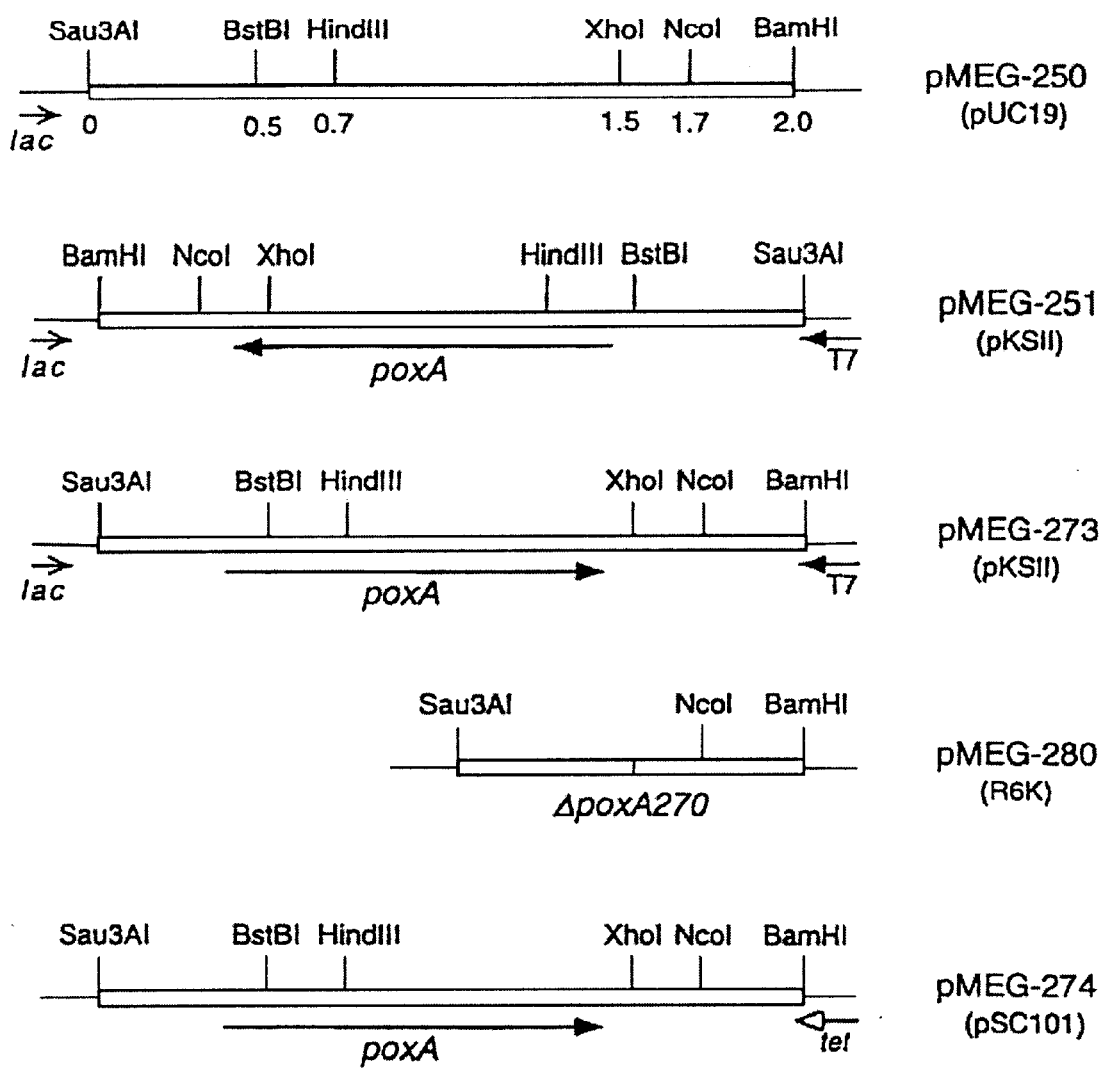

FIG. 4 is a diagram of partial restriction endonuclease maps of the poxR insert of plasmids pMEG-250, pMEG-251, pMEG-273, pMEG-280, and pMEG-274. The position of cleavage sites for some restriction endonucleases are shown. The direction of transcription of the poxR gene is indicated by the arrow. The plasmids from which each plasmid was derived is shown in parentheses underneath the plasmid name.

Figure 5:
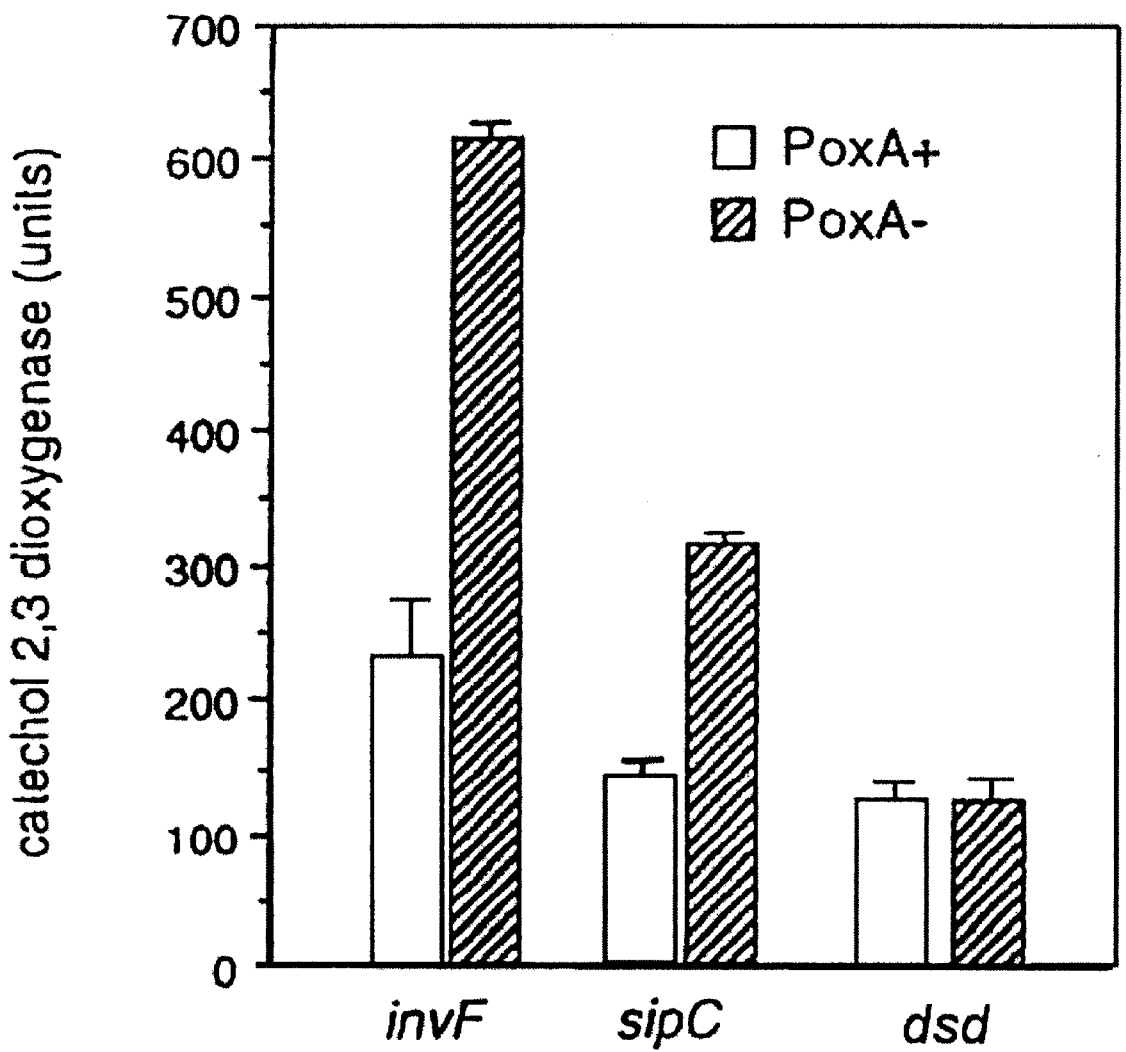

FIG. 5 is a graph of the effect of poxR mutation on invF and sipC gene expression. The expression was measured in units of catechol 2,3 dioxygenase, the product of the xylE reporter gene which was fused, in separate strains, to the chromosomal invF, sipC and asd genes. The poxR mutation was introduced in these strains by P22 transduction as described in the Example 4. Units are expressed as picomoles of catechol 2,3 dioxygenase per mg of protein$\times 10^2$.

FIGS. 6A and 6B show the nucleotide sequence of poxR gene (SEQ ID NO:1) and the deduced amino acid sequence of the encoded poxR protein (SEQ ID NO:2). The deduced amino acid sequence encoded by a partial second open reading frame (ORF2) is also shown (SEQ ID NO:3). The nucleotide sequence starts with the Sau 3AI site and ends at the Bam HI site. The putative Shine-Dalgarno sequences upstream of the open reading frames are at nucleotides 334–338 for poxR and nucleotides 1536–1540 for ORF2. The predicted ATG start codons begin at nucleotide 345 for poxR and nucleotide 1548 for ORF2.

DETAILED DESCRIPTION OF THE INVENTION

Disclosed are bacteria having virulence attenuated by a mutation to the regulatory gene poxR. Also disclosed is a method of producing bacteria having virulence attenuated by mutating to the regulatory gene poxR. Such bacteria are useful for inducing an immune response in an animal against virulent forms of the bacteria with reduced risk of a virulent infection. Such bacteria are also useful to allow use of normally virulent bacteria as research tools with reduced risk of virulent infection. In a preferred embodiment, poxR attenuated bacteria can be used as a vaccine to induce immunoprotection in an animal or human against virulent forms of the bacteria. The disclosed bacteria can also be used as hosts for the expression of heterologous genes and proteins. Attenuated bacteria with such expression can be used, for example, to deliver and present heterologous antigens to the immune system of an animal or human. Such presentation on live bacteria can lead to improved stimulation of an immune response by the animal to the antigens.

The poxR gene, which is referred to in the literature as poxA (Van Dyk et al. (1987)), is a regulatory gene affecting expression of pyruvate oxidase (Chang and Cronan (1982)). Pyruvate oxidase itself is encoded by the gene poxB (Chang and Cronan (1983)). Because mutants defective in poxB did not exhibit most of the various phenotypes observed in poxA mutants, we concluded that poxR is a regulatory gene having effects other than those resulting from a decrease in poxB expression. The regulatory nature of poxA leads us to rename the gene poxR.

The pyruvate oxidase of *Escherichia coli* is a peripheral membrane protein that catalyses the oxidative decarboxylation of pyruvate to acetate and $CO_2$ (Gennis and Hager, *The enzymes of biological membranes*, Volume 2 (Martonosi, ed., New York, N.Y., 1976), pages 493–504). Under laboratory conditions, this enzyme is not essential and conversion of pyruvate to acetate is considered wasteful of energy, compared with its conversion to acetyl coenzyme A (Gennis and Stewart, *Escherichia coli and Salmonella*, Volume 1 (Neidhardt, ed., ASM Press, Washington, D.C., 1996), pages 217–261). Pyruvate oxidase has been of interest primarily as a model for studying protein-lipid interaction. The enzyme is a water-soluble tetramer of 62 kDa identical subunits (Gennis and Stewart, 1996). It requires thiamine pyrophosphate, flavin adenine dinucleotide, and $Mg^{2+}$ as cofactors (Gennis and Hager (1976); Bertagnolli and Hager, *J. Biol. Chem.* 266:10168–10173 (1991); Bertagnolli and Hager, *Arch. Biochem. Biophys.* 300:364–371 (1993)). In the presence of the substrate and cofactors, the enzyme undergoes conformational changes and binds to *E. Coli* membrane vesicles and to phospholipid vesicles (Russell et al., *J. Biol. Chem.* 252:7883–7887 (1977); Schrock and Gennis, *Biochim. Biophys. Acta* 614:215–220 (1980)). This peripheral membrane binding is necessary for the terminal transfer of electron to ubiquinone-8 which is dissolved in the lipid bilayer (Grabau and Cronan, *Biochemistry* 25:3748–3751 (1986); Koland et al., *Biochemistry* 23:445–453 (1984)).

The poxR gene has other regulatory effects as evidenced by the pleiotropic phenotype of poxR mutants. Observed effects include reduced pyruvate oxidase activity, reduced growth rate, hypersensitivity to the herbicide sulfometuron methyl, to α-ketobutyrate and to amino acid analogs, and failure to grow in the presence of the host antimicrobial peptide, protamine. The structural gene for pyruvate oxidase, poxB, has been located at min 18.7 on the *E. coli* genetic map (Chang and Cronan (1983)).

A. poxR Genes

The poxR gene of *Salmonella typhimurium* was cloned as described in Example 1. The disclosed poxR gene (SEQ ID NO: 1), and nucleic acids derived from the poxR gene, can be used in the disclosed methods to mutate the poxR gene in a bacterial cell. The poxR gene, and nucleic acids derived from the poxR gene, can also be used to identify, map, and clone other poxR genes and genes homologous to poxR. The poxR gene, and nucleic acids derived from the poxR gene, can also be used to determine the structure of poxR mutants by, for example, Southern blotting or Northern blotting. The poxR gene can also be used to produce poxR protein, using, for example, recombinant DNA expression techniques. Nucleic acids derived from the poxR gene can also be used as specific probes or primers for use in, for example, the polymerase chain reaction (PCR) or related amplification methods, nucleic acid sequencing, detection of the presence or absence of specific poxR sequences in nucleic acid samples. These and many other techniques for the general use of nucleotide and gene sequences are known and can be practiced using the disclosed poxR gene and nucleic acids derived from the poxR gene. It is preferred that the disclosed poxR gene be used to mutate the poxR genes of bacterial cells and to clone other poxR genes. An example of the use of the disclosed poxR gene for mutating the poxR gene in a bacterial cell is described in Example 3.

The poxR protein (SEQ ID NO:2) encoded by the poxR gene can be used to produce antibodies immunoreactive to the poxR protein. Such antibodies can be used, for example, to identify or detect poxR protein, peptides derived from the poxR protein, or proteins related to the poxR protein, in a method such as Western blotting. Such antibodies can also be used to clone, or to identify clones, of poxr, genes homologous to poxR, or other related genes. Methods for the production of antibodies, and numerous techniques for their use, are known. Numerous examples of these are described in Johnstone and Thorpe, *Immunochemistry in Practice*, Second Edition (Blackwell Scientific Publications, 1987).

As used herein "gene" refers to a nucleic acid segment encoding a protein or transcription product. As used herein, this term can refer to nucleic acid segments containing only a coding region, or to nucleic acid segments containing a coding region and any associated expression sequences such as a promoter, a translation initiation sequence, and regulatory sequences. The term gene can refer to both naturally occurring genes and those produced by genetic manipulation, such as recombinant DNA technology or mutagenesis.

As used herein "homologous" in reference to genes, other nucleic acid sequences, and proteins, refers to genes, other nucleic acid sequences, and proteins that are similar to each other, respectively. As a practical matter, homologous genes or proteins are identified on the basis of moderate to high sequence identity between the genes or proteins. Homology can also be identified by the presence of highly conserved subsequences in the genes or proteins (even where overall sequence similarity or identity is low). Such conserved subsequences are typically referred to as consensus sequences or domains. As used herein, a "homolog" of a first gene, other nucleic acid sequence, or protein refers to a second gene, other nucleic acid sequence, or protein, respectively, that is homologous to the first gene, other nucleic acid sequence, or protein. Preferred homologs of the poxR gene or the poxR protein are naturally occurring genes and proteins. Such genes and proteins are preferred targets of mutation in the disclosed method since a preferred purpose of such mutants is to attenuate the natural virulence of the bacteria in which the homologous gene (encoding the homologous protein) is present.

A preferred means of determining if a gene, other nucleic acid sequence, or protein is homologous to the poxR gene, a nucleic acid sequence derived from the poxR gene, or the poxR protein is to determine if the nucleotide or amino acid sequences of the nucleic acids or proteins have a sequence identity with a reference sequence of at least a specified threshold. As used herein, percent nucleotide or amino acid sequence identity is calculated as the percentage of aligned amino acids that match the reference sequence, where the sequence alignment has been determined using the alignment algorithm of Dayhoff et al., *Methods in Enzymology* 91: 524–545 (1983).

Preferred homologs of the poxR gene have a nucleotide sequence identity with nucleotides 345 to 1319 of SEQ ID NO:1 of greater than 40%, such as at least 50% nucleotide sequence identity, at least 60% nucleotide sequence identity, or at least 70% nucleotide sequence identity. Preferably, homologs of the poxR gene have at least 80% nucleotide sequence identity; more preferably, at least 90% nucleotide sequence identity; and most preferably, at least 95% nucleotide sequence identity with nucleotides 345 to 1319 of SEQ ID NO:1.

Other preferred homologs of the poxR gene encode an amino acid sequence having an amino acid sequence identity with SEQ ID NO:2 of greater than 40%, such as at least 50% amino acid sequence identity, at least 60% amino acid sequence identity, or at least 70% amino acid sequence identity. Preferably, homologs of the poxR gene encode an amino acid sequence having at least 80% amino acid sequence identity; more preferably, at least 90% amino acid sequence identity; and most preferably, at least 95% amino acid sequence identity with SEQ ID NO:2.

Preferred homologs of the poxR protein have an amino acid sequence identity with SEQ ID NO:2 of greater than 40%, such as at least 50% amino acid sequence identity, at least 60% amino acid sequence identity, or at least 70% amino acid sequence identity. Preferably, homologs of the poxR protein have at least 80% amino acid sequence identity; more preferably, at least 90% amino acid sequence identity; and most preferably, at least 95% amino acid sequence identity with SEQ ID NO:2.

Although poxR gene was identified 15 years ago, molecular and functional data on the gene and gene product are lacking. As disclosed herein, the poxR gene of *S. typhimurium* was cloned and the nucleotide sequence was determined (Example 1). Comparison of the amino acid sequence derived from the poxR gene to the available databases indicated high homology to an uncharacterized ORF of *E. coli* 94 min region (91% identity; 96% similarity) and *Haemophilus influenzae* (65% identity, 79% similarity). The poxR gene product was also characterized (Example 2) and the influence of a poxR mutation on *S. typhimurium* “pathogenicity island I”.

B. Bacterial Cells

Any bacterial cells in which a mutation to poxR, or a mutation to a gene in the cell that is homologous to poxR, is suitable for use in the disclosed methods and composition. Preferred bacterial cells are those that colonize, infect, or otherwise grow in or on animals. Particularly preferred are bacterial cells that colonize, infect, or grow in either or both the gastrointestinal tract or respiratory tract. Also preferred are bacterial cells that colonize, infect, or grow in the urogenital tract. Some preferred bacterial cells belong to one of the families Enterobacteriaceae, Micrococcaceae, Vibrionaceae, Pasteurellaceae, Mycoplasmataceae, or Rickettsiaceae. Within these families, preferred bacterial cells belong to one of the genera Salmonella, Shigella, Escherichia, Enterobacter, Serratia, Proteus, Yersinia, Citrobacter, Edwardsiella, Providencia, Klebsiella, Haffnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, or Ehrlichia. Particular preferred bacterial cells are those that belong to the family Enterobacteriaceae.

Preferred bacterial cells belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Ricketsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Camylobacter, Arcobacter, Wolinella, Heliobacter, Achomobacter, Acinetobacter, Agrobacterium, Alcaligenes, Chryseomonas, Comamonas, Eikenella, Flavimonas, Flavobacterium, Moraxella, Oligella, Pseudomonas, Skewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thernoactinomycetes, Mycobacterium, Treponema, Borrelia, Leptospira, or Chlamydiae.

Particularly preferred are bacterial cells that belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, or Morganella. Most preferred are bacterial cells that belong to one of the genera Salmonella or Escherichia.

It is preferred that bacterial cells having a poxR mutation also contain other features which attenuate their virulence and increase their immunogenicity. For example, strains of different Salmonella serotypes can be rendered avirulent by methods known to those skilled in the art, for example, 1) by introducing mutations that impose a requirement for aromatic amino acids and vitamins derived from precursors in this pathway (Stocker et al., *Dev. Biol. Stand.* 53:47–54 (1983), Hoiseth et al., *Nature* 291(5812):238–239 (1981)), 2) by mutating genes for global regulators such as cya and crp (Curtiss and Kelly, *Infect. Imm.* 55:3035 (1987)), phoP (Miller et al., *Proc. Natl. Acad. Sci. USA* 86:5054–8 (1989), Galán and Curtiss, *Microb. Pathogen.* 6:433–443 (1989)), and ompR (Dorman et al., *Infect. Immun.* 57:2136–40 (1989)), 3) by mutating genes for lipopolysaccharide (LPS) synthesis, such as by galE (Germanier and Furer, *Infect. Immun.* 4:663–73 (1971), Germanier and Furer, *J. Infect. Dis.* 131:553–8 (1975)), although this alone may be insufficient (Hone et al., *Infect. Immun.*56:1326–1333 (1988)), pmi (Collins et al., *Infect. Immun.* 59:1079–1085 (1991)), 4) by mutating genes needed for colonization of deep tissues, such as cdt (Kelly et al., *Infect. Immun.* 60:4881–4890 (1992); Curtiss et al., *Devel. Biol. Stand.* 82:23–33 (1994)), or 5) by preventing expression of genes for proteases required at high temperature, such as htrA (Johnson et al., *Mol. Microbiol.* 5:401–407 (1991). Strains possessing mutations in phoQ (Miller et al., *Proc. Natl. Acad. Sci. USA* 86:5054 (1989)) have the same phenotype as mutations in phoP. Strains with mutations in either phoP or phoQ are referred to herein collectively as phoP mutants. It is preferred that mutations in the above described genes be introduced as deletions since this will preclude reversion mutations and enhance the safety of the strains containing them. Subsequent to the discovery that Salmonella strains with mutations in the genes described above are avirulent and immunogenic, it was observed that many of these strains exhibited, after oral administration, nearly wild-type abilities to invade and persist in the GALT and to colonize other lymphoid tissues such as mesenteric lymph nodes, liver, and spleen, but without causing disease symptoms. As a consequence, these attenuated strains are capable of stimulating strong mucosal, systemic and cellular immune responses in irimmunized animal hosts that confer protective immunity to challenge with virulent wild-type Salmonella strains.

Any Salmonella having a poxR mutation can be endowed with the ability to express important colonization or virulence antigens from other bacterial, viral, mycotic and parasitic pathogens at a high level within an immunized animal host (Clements, *Pathol. Immunopathol. Res.* 6:137–146 (1987); Dougan et al., *Parasite Immun.* 9:151–60 (1987); Chatfield et al., FEMS *Immunol. Med. Microbiol.* 7:1–7 (1993); Curtiss et al., in *Virulence mechanisms of bacterial pathogens*, (Roth, American Society for Microbiology, Washington, D.C., 1988) pages 311–328; Curtiss et al., *Dev. Biol. Stand.* 82:23–33 (1994); Doggett and Curtiss, *Adv. Exp. Med. Biol.* 327:165–73 (1992); Schödel, *Semin Immunol.* 2:341–9 (1990)).

C. Method of Producing Bacterial Cells Having Attenuated Virulence

In *S. typhimurium*, mutations in several global regulatory loci including cya/crp (Curtiss and Kelly (1987)), phoPQ (Miller et al. (1989)), rpoS (Robbe-Saule et al., FEMS *Microbiol. Lett.* 126(2):171–176 (1995)) have been associated with reduced virulence. By examining the role of the poxR gene in the pathogenicity of *S. typhimurium*, it was discovered that mutation of poxR reduces the virulence of the cells.

The disclosed method of producing a bacterial cell having attenuated virulence involves mutating the poxR gene, or its homolog, in the bacterial cell. The mutation can be of any type and have any effect on expression of the poxR gene or on the activity of the poxR protein so long as the virulence of the bacterial cell is reduced. Preferred mutations are those that prevent or reduce transcription of the poxR gene, prevent or reduce translation of poxR mRNA, or which mutate the encoded poxR protein so that it is no longer active or has reduced activity. In this context, activity of a mutant poxR protein refers to its phenotypic effect on virulence. Numerous general methods for mutating genes in bacterial cells are known and most are suitable for making poxR mutants. Most preferred are deletion mutations that result in the production of a significantly truncated poxR protein. Such mutations are stable. An example of the disclosed method involving the production of such a deletion mutation is described in Example 3.

Deletion mutations of poxR can be introduced into the bacterial chromosome using well known recombinant DNA techniques. For example, the poxR gene can be first cloned onto a suicide vector. The replication of the suicide vector is dependent on a complementing gene on the chromosome. When the suicide vector is transferred to a strain lacking the complementing gene, the only means of maintaining the suicide vector is by recombination integrating the suicide vector into the host chromosome. The presence of the poxR gene on the suicide vector results in homologous recombination of the suicide vector into the corresponding gene on the chromosome. This integration will result in a deletion in the gene of chromosomal poxR gene if the wild-type poxR gene on the suicide vector has been altered by deletion of internal regions of the gene prior to integration. This can be accomplished by either restriction enzyme digestion or inverse PCR amplification. The vector-borne poxR gene is thus inactivated while leaving sufficient flanking DNA to allow recombination into the chromosome. The defined deletion produced in the suicide vector can be designed to provide a convenient restriction enzyme cloning site allowing the insertion of any foreign gene, such as a gene encoding an antigen. After the initial single recombination event integrating the suicide vector into the chromosome, a second recombinational event can be selected for by selection against, for example, a tetracycline element on the suicide vector on media containing fusaric acid (Bochner et al., *J. Bactetiol.* 143:926 (1980)). Alternative mobilizable suicide vectors are also available utilizing sucrose counter selection for the introduction of defined deletions into Salmonella and other gram negative bacteria (Kaniga et al., *Gene* 109:137–141 (1991)). This results in the replacement of the wild-type allele with the deleted gene containing the desired insert. These methods have been used to produce defined deletions and insertion of foreign genes into the chromosome of Salmonella strains (Chatfield et al., *Vaccine* 10:53–60 (1992)). A mutation in the poxR gene can also be generated by transformation using linear DNA molecules carrying a selectable marker inserted in poxR.

It is preferred that the poxR mutation be made by genetic manipulation. As used herein, genetic manipulation refers to a purposeful manipulation of the genome of a bacterial cell directed to altering a specific gene. This can be accomplished, for example, by specifically directing or targeting mutagenesis to a specific gene, or by creating a pool of random mutants and specifically selecting or screening for those in which the poxR gene is mutated. It is intended that genetic manipulation does not encompass genetic changes that occurred naturally, that is, which did not arise through purposeful human intervention or action directed to altering a specific gene. Thus, as used herein, bacterial cells in which the poxR gene has been mutated by genetic manipulation do not include those cells in which the mutation occurred in nature by natural processes.

Virulence of the disclosed bacterial cells can be assessed by, for example, using the chick model described in Example 6, or the mouse model described in Examples 7 and 8. As used herein, attenuated virulence refers to a reduction in virulence of bacteria relative to a reference bacteria of the same type. It is preferred that the reference bacteria is a wild-type bacteria. Most preferably, the reference bacteria is the parent strain from which a poxR mutant was generated. Avirulent does not mean that a bacterial cell of that genus or species can not ever function as a pathogen, but that the particular bacterial cell being used is avirulent with respect to the particular animal being treated. The bacterial cell may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart.

D. Method of Inducing an Immune Response in an Aninmal

The disclosed bacterial cells having attenuated virulence are preferably used to induce an immune response in an animal. As used herein, an immune response refers to the production of antibodies which are immunoreactive to bacterial cells used to induce the response, or to one or more antigens, or nucleic acid encoding an antigen, which are delivered by the bacterial cells. The antibody so produced may belong to any of the immunological classes, such as immunoglobulins A, D, E, G or M. Of particular interest is the production of immunoglobulin A (IgA) since this is the principle immunoglobulin produced by the secretory system of warm-blooded animals. The disclosed bacterial cells are likely to produce a broad range of other immune responses in addition to such IgA formation, for example, cellular and humoral immunity.

The immune response induced is preferably, but need not be, immunoprotective. As used herein, an immunoprotective immune response is an immune response which reduces the growth, infectivity, pathenogeneity, or viability of an infectious agent in an animal. Most preferred is an immunoprotective immune response which prevents growth, infectivity, pathenogeneity, or viability of an infectious agent in an animal.

The disclosed bacterial cells having a poxR mutation can be used to induce an immune response to related bacterial cells (since the disclosed bacterial cells will present their native antigens to a host animal when administered), or, preferably, the disclosed cells can be used as an antigen delivery system. As used herein, the terms antigen delivery system and antigen delivery bacteria refer to bacterial cells that produce an antigen or that harbor a vector encoding an antigen. In one preferred embodiment of an antigen delivery system using the disclosed bacterial cells, pathogenic bacterial cells that attach to, invade and persist in the gut-associated lymphoid tissue (GALT) or bronchial-associated lymphoid tissue (BALT), and that have a poxR mutation are used as a carrier of a gene product which is used for stimulating immune responses against a pathogen or allergen.

Salmonella having a poxR mutation can be used to protect animals and humans against Salmonella infection. To be useful, such strains need not express any foreign antigen. Salmonella having a poxR mutation and expressing protective antigens from bacterial, viral, mycotic and parasitic pathogens that are efficacious in inducing immunities to protect against infections by these pathogens are preferred for inducing an immune response. Salmonella having a poxR mutation as well as containing other mutations which reduce virulence or which are otherwise of reduced virulence are also preferred.

Shigella or an enteroinvasive *E. coli* having a poxR mutation can be useful in antigen delivery systems since invasion into colonic mucosa could stimulate lymphoid tissues adjacent to the colon, so as to stimulate a strong mucosal immune response in the reproductive tract. Rectal immunization can be effective because of anatomical features such as the proximity of lymph nodes and lymphatics to the colon.

Antigens. Live bacteria having a poxR mutation can be used to deliver any product that can be expressed in the bacteria. Preferred expression products for this purpose are antigens. For example, antigens can be from bacterial, viral, mycotic and parasitic pathogens, to protect against bacterial, viral, mycotic, and parasitic infections, respectively; gametes, provided they are gamete specific, to block fertilization; and tumor antigens, to halt cancers. It is specifically contemplated that antigens from organisms newly identified or newly associated with a disease or pathogenic condition, or new or emerging pathogens of animals or humans, including those now known or identified in the future, can be used with the disclosed bacterial cells and methods. Antigens for use in the disclosed bacterial cells are not limited to those from pathogenic organisms. The selection and recombinant expression of antigens has been previously described by Schödel (1992) and Curtiss (1990). It is preferred that a gene for expression in the disclosed bacterial cells be operably linked to a promoter of any gene of the type III secretion system, preferably a promoter of a sip (ssp) gene, a yop gene, a ipa gene, or a hrp gene. It is also preferred that an expression product for the disclosed bacterial cells be expressed as a fusion to a Sip (Ssp) protein, a Yop protein, a Ipa protein, or a Hrp protein. Such a fusion is preferably expressed using the natural promoter with which the protein is expressed. Immunogenicity of the bacterial cells can be augmented and/or modulated by constructing strains that also express genes for cytokines, adjuvants, and other immunomodulators.

Some examples are microorganisms useful as a source for antigen are listed below. These include antigens for the control of plague caused by *Yersinia pestis* and other Yersinia species such as *Y. pseudotuberculosis* and *Y. enterocolitica*, of gonorrhea caused by *Neisseria gonorrhoea*, of syphilis caused by *Treponema pallidum*, and of venereal diseases as well as eye infections caused by *Chlamydia trachomatis*. Species of Streptococcus from both group A and group B, such as those species that cause sore throat or heart diseases, *Neisseria meningitidis, Mycoplasma pneumoniae* and other Mycoplasma species, *Hemophilus influenza, Bordetella pertussis, Mycobacterium tuberculosis, Mycobacterium leprae*, Bordetella species, *Escherichia coli, Streptococcus equi, Streptococcus pneumoniae, Brucella abortus, Pasteurella hemolytica* and *P. multocida, Vibrio cholera*, Shigella species, Borrellia species, Bartonella species, *Heliobacter pylori*, Campylobacter species, Pseudomonas species, Moraxella species, Brucella species, Francisella species, Aeromonas species, Actinobacillus species, Clostridium species, Rickettsia species, Bacillus species, Coxiella species, Ehrlichia species, Listeria species, and *Legionella pneumophila* are additional examples of bacteria from which antigen genes could be obtained. Viral antigens can also be used with the disclosed bacterial cells. Viral antigens can also be used, including antigens from either DNA or RNA viruses, for example from the classes Papovavirus, Adenovirus, Herpesvirus, Poxvirus, Parvovirus, Reovirus, Picornavirus, Myxovirus, Paramyxovirus, or Retrovirus. Antigens of pathogenic fungi, protozoa and parasites can also be used.

The antigen can also be an allergen of the host such as antigens from pollen and animal dander. Such an antigen can be used in the disclosed bacterial cells in an exposure regimen designed to specifically desensitize an allergic host.

Recombinant Salmonella encoding foreign antigens are capable of stimulating strong mucosal, systemic and cellular immune responses against the foreign antigens and thus against the pathogen that is the source of the foreign antigen. It is not necessary that the antigen gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier bacteria so that a peptide comprising only 75, or even 10, amino acid residues is produced by the cellular mechanism of the host cell. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus a gene as defined here is any unit of heredity capable of producing an antigen. The gene may be of chromosomal, plasmid, or viral origin.

Multiple antigens can also be expressed by a Salmonella strain having a poxR mutation. In addition, antigens, or even parts of antigens, that constitute a B cell epitope or define a region of an antigen to which an immune response is desired, can be expressed as a fusion to a carrier protein that contains a strong promiscuous T cell epitope and/or serves as an adjuvant and/or facilitates presentation of the antigen to enhance, in all cases, the immune response to the antigen or its component part. This can easily be accomplished by genetically engineering DNA sequences to specify such fusions for expression by the disclosed bacterial cells. Fusion to tenus toxin fragment C, CT-B, LT-B and hepatitis virus B core are particularly useful for these purposes, although other epitope presentation systems are well known in the art.

In order for the disclosed bacteria to be most effective in immunizing an individual, it is preferred that the antigenic material be released in such a way that the immune system of the vaccinated animal can come into play. Therefore the poxR mutant bacteria must be introduced into the animal. In order to stimulate a preferred response of the GALT or BALT cells as discussed previously, introduction of the bacteria or gene product directly into the gut or bronchus is preferred, such as by oral administration, intranasal administration, gastric intubation or in the form of aerosols, although other methods of administering the antigen delivery bacteria, such as intravenous, intramuscular, subcutaneous injection or intramammary, intrapenial, intrarectal, or vaginal administration, is possible.

Antigen Delivery Compositions. A preferred use of the disclosed bacteria is as vaccines for stimulating an immune response to the delivered antigens. Oral immunization in a suitable animal host with live recombinant Salmonella having a poxR mutation leads to colonization of the gut-associated lymphoid tissue (GALT) or Peyer's patches, which leads to the induction of a generalized mucosal immune response to both Salmonella antigens and any foreign antigens synthesized by the recombinant Salmonella (Curtiss et al., *Adv. Exp. Med. Biol.* 251:33–47 (1989)). Further penetration of the bacteria into the mesenteric lymph nodes, liver and spleen augments the induction of systemic and cellular immune responses directed against Salmonella antigens and the foreign antigens made by the recombinant Salmonella (Doggett and Curtiss (1992)). Thus the use of recombinant Salmonella for oral immunization stimulates all three branches of the immune system, particularly important when immunizing against infectious disease agents which colonize on and/or invade through mucosal surfaces.

By vaccine is meant an agent used to stimulate the immune system of a living organism so that an immune response occurs. Preferably, the vaccine is sufficient to stimulate the immune system of a living organism so that protection against future harm is provided. Such protection is referred to herein as immunoprotection. Immunization refers to the process of inducing a continuing high level of antibody and/or cellular immune response in which T-lymphocytes can either kill the pathogen and/or activate other cells (for example, phagocytes) to do so in an organism, which is directed against a pathogen or antigen to which the organism has been previously exposed. Although the phrase "immune system" can encompass responses of unicellular organisms to the presence of foreign bodies, as used herein the phrase is restricted to the anatomical features and mechanisms by which a multi-cellular organism responds to an antigenic material which invades the cells of the organism or the extra-cellular fluid of the organism. The antibody so produced may belong to any of the immunological classes, such as immunoglobulins A, D, E, G or M. Of particular interest are recombinant poxR mutant bacteria which stimulate production of immunoglobulin A (IgA) since this is the principle immunoglobulin produced by the secretory system of warm-blooded animals, although the disclosed bacteria for use as vaccines are not limited to those which stimulate IgA production. For example, bacterial vaccines of the nature described herein are likely to produce a broad range of other immune responses in addition to IgA formation, for example, cellular and humoral immunity. Immune responses to antigens are well studied and widely reported. A survey of immunology is given in Barrett, *Textbook of Immunology*, Fourth Edition, (C.V. Mosby Co., St. Louis, Mo., 1983), Sites et al., *Basic and Clinical Immunology* (Lange Medical Books, Los Altos, Calif., 1994), and Orga et al., Handbook of Mucosal Immunology (Academic Press, San Diego, Calif., 1994). Mucosal immunity is also described by McGhee and Mestecky, *The Secretory Immune System*, Ann. N.Y. Acad. Sci., Volume 409 (1983).

An individual treated with a vaccine comprising the disclosed bacterial cells is defined herein as including all vertebrates, for example, mammals, including domestic animals and humans, various species of birds, including domestic birds, particularly those of agricultural importance. Preferably, the individual is a warm-blooded animal.

The dosages of the disclosed bacterial cells required to elicit an immune response will vary with the antigenicity of the cloned recombinant expression product and need only be a dosage sufficient to induce an immune response typical of existing vaccines. Routine experimentation will easily establish the required dosage. Typical initial dosages of bacterial vaccine for oral administration could be $1 \times 10^7$ to $1 \times 10^{11}$ CFU depending upon the size and age of the individual to be immunized. Administering multiple dosages can also be used as needed to provide the desired level of protective immunity. The pharmaceutical carrier in which the bacterial vaccine is suspended can be any solvent or solid material for encapsulation that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc or sucrose, or animal feed. Adjuvants may be added to enhance the antigenicity if desired. When used for administering via the bronchial tubes, the bacterial vaccine is preferably presented in the form of an aerosol.

Immunization with a pathogen-derived gene product can also be used in conjunction with prior immunization with a derivative of a pathogenic bacteria which has a poxR mutation and which acts as a carrier to express the pathogen-derived gene product. Such parenteral immunization can serve as a booster to enhance expression of the secretory immune response, once the secretory immune system has been primed to that pathogen-derived gene product, by immunization with the recombinant bacteria expressing the pathogen-derived gene product in order to stimulate the lymphoid cells of the GALT or BALT. The enhanced response is known as a secondary, booster, or anamnestic response and results in prolonged immune protection of the host. Booster immunizations may be repeated numerous times with beneficial results.

Although it is preferred that the disclosed bacterial cells adapted for antigen delivery be administered by routes that stimulate a mucosal immune response, namely oral, intranasal, intravaginal, and interrectal, these bacterial cells can also be delivered intramuscularly, intravenously, and in other parenteral routes. Administration of bacterial cells can also be combined with parenteral administration of purified antigenic components.

Genetic Immnunization. The disclosed poxR mutant bacterial cells can also be used to deliver DNA in vivo, and thereby induce an immune response. Delivery of DNA for inducing an immune response is referred to as genetic immunization. For this purpose, it is preferred that such DNA encode an antigen. Preferably, the DNA is in the form of a transfer vector. A bacterial cell having a poxR mutation can harbor a vector for transfer to, and expression in, a cell in an animal or human into which the bacterial cell is placed. As used herein, a transfer vector is an expression vector which can be transferred from a bacterial cell having a poxR mutation into a cell, and which directs the expression of a gene encoded by the transfer vector. It is intended that the transfer vector can contain any gene for expression, including genes encoding antigens, immunomodulators, enzymes, and expression products which regulate gene expression or cellular activity in the recipient cell.

Preferred recipients for transfer vectors are cells of animal or human hosts. For this purpose, bacterial cells having a poxR mutation and a transfer vector can be administered to an animal host. It is preferred that the bacterial cells invade host cells in order to deliver the transfer vector. For expression of genes on the transfer vector in recipient cells, it is preferred that the genes be operatively linked to expression control sequences operable in the recipient cell. For example, where the recipient cell is an animal or human cell, it is preferred that the genes be operatively linked to a promoter functional in the animal or human.

Transfer vectors may also contain replication sequences operable in the recipient cell. This would allow replication of the transfer vector, resulting in increased or longer expression of genes present on the transfer vector. Transfer vectors are especially useful for expression of antigens and other proteins that need to be glycosylated or post-translationally modified in a eukaryotic cell. In this way a bacterial cell having a poxR mutation can be used for delivery of a protein requiring eukaryotic processing by expressing the protein from a transfer vector.

An example of a vector suitable for use as a transfer vector in a bacterial cell having a poxR mutation is described by Sizemore et al., *Science* 270:299–302 (1995). Sizemore et al. used a construct expressing β-galactosidase under the control of the immediate early cytomegalovirus promoter and observed the expression of (β-galactosidase in eukaryotic cells following lysis of a Δasd Shigella strain due to DAPless death.

A preferred use for transfer vectors is in a live bacterial antigen delivery system for stimulation of an immune response in a host animal. For this purpose it is preferred that the bacteria is Salmonella, Shigella, Yersinia, or invasive Escherichia that would invade and then lyse to liberate a transfer vector designed for expression in cells of the animal or human host. This can be useful in stimulating an immune response for viruses, parasites or against gamete antigens where the antigens are normally glycosylated or post-translationally modified in some way that can only be accomplished when the antigen product is synthesized within the eukaryotic cell.

The efficiency of transfer of a transfer vector or other DNA for genetic immunization can be improved by including an endA mutation, mutations in recBC (with or without sbc suppressor mutations), and/or mutations in other nuclease genes. Such mutations can reduce degradation of the transfer vector or other DNA upon lysis of the bacterial cell. It is also possible to influence the host cell type and the mucosal surface to which the bacterial cell containing the transfer vector or other DNA would adhere to and invade. This can be achieved by blocking or turning on the expression of specific adhesins and/or invasins.

Many vectors are known for genetic immunization or introduction into cells in an animal or human. Such vectors can be used as transfer vectors in bacterial cells having a poxR mutation. In this case, the bacterial cell having a poxR mutation provides a useful means for introducing such vectors into cells. Preferred promoters for expression of genes on transfer vectors are adenovirus, herpes virus and cytomegalovirus promoters. Expression of the gene can also be increased by placing a bacterial promoter upstream of the eukaryotic promoter, so that the bacterial strain would already express some of the expression product. This expression product would be liberated upon lysis of the bacterial cell.

EXAMPLES

The bacterial strains and plasmids used or made in the following examples and their sources are listed in Table 1. Strains were grown in L broth or on L agar (Lennox, *Virology* 1:190–206 (1955)) or Antibiotic No. 2 (Difco, Detroit, Mich.). When required, antibiotics were added to the growth medium at the following concentration: Kanamycin, 50 µg/ml; ampicillin, 100 µg/ml; streptomycin, 100 µg/ml; tetracycline, 12.5 µg/ml.

TABLE 1

Bacterial strains.

| Strain | Relevant genotype | Reference/Source |
|---|---|---|
| *S. typhimurium* | | |
| SMS401 | poxA401::Tn10 | Van Dyk et al. (1987) |
| SB164 | invF::xylE | Kaniga et al., Mol. Microbiol. 13(4):555–568 (1994) |
| SB164N | invF::xylE poxR401::Tn10 | Example 4 |
| SB227 | sipC::xylE | Kaniga et al., J. Bacteriol. 177(24):7078–7085 (1995) |
| SB227N | sipC::xylE poxR401::Tn10 | Example 4 |
| x3761 | wild-type UK-1 | Curtiss, laboratory collection |
| MGN-762s | ΔphoPQ23 | S. Tinge (unpublished) |
| MGN-791s | poxR401::Tn10 | Example 1 |
| MGN-816s | ΔpoxR401 | Example 1 |

TABLE 1-continued

Bacterial strains.

| Strain | Relevant genotype | Reference/Source |
|---|---|---|
| MGN-824s | ΔphoPQ23 Δasd729::xylE | Example 4 |
| MGN-939s | ΔpoxR401 (pMEG-250) | Example 1 |
| MGN-1036s | ΔpoxR270 | Example 3 |
| MGN-1055s | ΔpoxR270 Δasd729::xylE | Example 4 |
| *E. coli* | | |
| MGN-617 | thi thr leu tonA lacY supE λpir recA::RP4-2-Tc::Mu (KmR) Δasd1 | K. Roland (unpublished) |
| CC118λpir | araD139 Δ (ara-leu)7697 ΔlacX74 galK ΔphoA20 galE recA1 rpsE argE (Am) rpoB thi λpir | de Lorenzo et al., J. Bacteriol. 172(11):6568–6572 (1991) |

Example 1
Cloning of the poxR Gene by Genetic Complementation

Recombinant DNA techniques were performed according to standard procedures (Sambrook et al., Molecular Cloning (Cold Spring Harbor Laboratory, Cold Spring Harbor, N.Y., 1989)). Transformation of plasmid DNA into *E. coli* and Salmonella strains by electroporation was carried out as described by O'Callaghan and Charbit (*Mol. Gen. Genet.* 223:157–160 (1990)) using an *E. coli* Gene Pulser apparatus (Bio-Rad Laboratories). poxR401::Tn 10 insertion was moved into *S. typhimurium* using P22HTint transduction as previously described (Galán et al., *J. Bacteriol.* 17:4338–4349 (1992)). poxA401::Tn10 allele (now referred to as poxR401::Tn10) was introduced into wild-type *S. typhimutium* UK-1 strain x3761 by P22 transduction using a P22 lysate grown on *S. typhimurium* SMS401, to generate strain MGN-791s. Bacteriophage P22HTint was used for the transductions (Schmeiger, *Mol. Gen. Genet.* 119:74–88 (1972)). Although poxR mutants grow slower than the wild-type parent (Chang and Cronan (1982)), this differential growth rate does not appear to be a strong phenotype. Unlike the LT2 derivative strains SMS401 which exhibits a hypersensitivity to α-ketobutyrate (AKB) (Van Dyk and LaRossa, *J. Bacteriol.* 165(2):386–392 (1986); Van Dyk et al. (1987)), it was found that *S. typhimutrium* UK-1 poxR401::Tn10 show a marginal sensitivity to AKB. Therefore, a range of bacteriological media was screened for substantial difference in growth rates between poxR mutants and isogenic wild-type. It was found that all poxR mutant derivatives of *S. typhimurium* produced microcolonies on Antibiotic No. 2 agar (AB2), as compared to LB agar media. A fusaric acid resistant derivative of MGN-791s was selected following Tn10 deletion to generate MGN-816s. Under the same conditions, the parental strain x3761 produced normal size colonies on both AB2 and LB agar plate. The poxR gene was then cloned by virtue of its ability to restore normal growth to a poxR defective strain on AB2 media.

A genomic library of wild-type *S. typhimurium* UK-1 strain x3761 in a pUC19-derived vector pNEB193 was used (obtained from Steve Tinge). This library was introduced into *S. typhimurium* strain MGN-816s by electroporation and selection on AB2 plate containing ampicillin. Among approximately 5,000 ampicillin-resistant microcolonies, one transformant, MGN-939s, exhibited a large colony morphology indicating that strain MGN-939s had acquired a DNA fragment capable of fully complementing the growth defect of the poxR mutant. The plasmid, designated pMEG-250 was purified and introduced into *E. coli* CC118 λpir. A partial restriction map of the 2 kilobase (kb) DNA insert in pMEG-250 was established (FIG. 4). To ensure that the complementation was solely due to cloned poxR and not to an unknown secondary mutation acquired during the selection, pMEG-250 was reintroduced into MGN-816s. All transformants were complemented to the large colony phenotype on AB2. This result strongly suggests that the 2 kb DNA fragment of UK-1 in pMEG-250 encodes an active poxR protein. Alternatively, the DNA fragment could also encode a suppressor of poxR, as the complementing pMEG-250 was a high copy plasmid. To address that possibility, a Southern blot analysis was performed on Cla I digested genomic DNA from wild-type x3761 and the transposon Tn10 insertion in poxR strain MGN-791s using labelled 2 kb insert from pMEG-250 as the probe. The probe hybridized to a single Cla I fragment in wild-type and to two Cla I fragments in poxR401::Tn10. The results confirmed that the 2 kb DNA fragment of pMEG 250 encodes the poxR gene.

The poxR-encoding fragment was re-cloned in the opposite orientation in relation to the plasmid encoded lac promoter, generating pMEG-251 and pMEG-273 (FIG. 4). Both pMEG 251 and pMEG 273 were able to complement a poxR401::Tn10 polar mutation. This indicates that the 2 kb DNA fragment carries a promoter sequence necessary for the expression of poxR. In the absence of antibiotic selection, the high copy pMEG-251 and pMEG-273 were unstable and were lost at a high frequency. Therefore, the poxR gene was established into a low copy pLG339 vector (a pSC101 derivative) to give pMEG-274 (FIG. 4). This plasmid was found to be stable in *S. typhimurium*.

Nucleotide sequence of the poxR gene. The 2 kb DNA fragment of plasmid pMEG-250 was sequenced on both strands. Nucleotide sequence determination was performed by ACGT, Inc. using double-stranded DNA as templates, and both strands were sequenced. The nucleotide sequence (FIG. 6; SEQ ID NO:1) was analyzed using the MacVector 5.0 software. Searches for homology in the available databases were performed using the BLAST program at the National Center for Biotechnology Information (Altschul et al., *J. Mol. Biol.* 215:403–410 (1990)). At the nucleotide level, the 2,008 bp fragment showed 81% identity to the min 94 region of *E. coli* chromosome including yjeA and yjeM, and 61% identity to *Haemophilus influenza* chromosome including the yjeA and yjbM genes. This is in agreement with the map position of poxR401::Tn10 determined in *S. typhimurium*. yjeA, yjeM and yjbM were identified during the automated sequencing of the genome of these organisms. Two open reading frames (ORF) were found in the 2,008 bp sequence. The first ORF, preceded by a putative Shine and Dalgarno (SD) sequence, starts at nucleotide 345 and encodes a polypeptide 325 amino acids with a predicted molecular mass of 36.8 kDa. Hydrophobicity analysis using the algorithm of Kyte and Doolittle indicated that poxR does not have a signal sequence or membrane-spanning domain, suggesting that poxR is a cytoplasmic protein. poxR showed 91% identity, 96% similarity to *E. coli* GenX (YjeA), a lysyl-tRNA synthatase homologue, and 65% identity, 79% similarity to GenX (YjeA) of *H. influenza*. YjeA has not been characterized at the molecular level, and no function has been ascribed to this protein in either organism. The second ORF, preceded by a putative SD sequence, starts at nucleotide 1548 and was truncated at nucleotide 2,008. This ORF was found to be homologous to *E. coli* YjeM (88% identity and 96% similarity). No function has been assigned to this protein in *E. coli*. Although the transposon Tn10 insertion has not been mapped, it is reasonable to assume, based upon the genetic complementation data, that the insertion took place in the poxR coding region, since the second ORF is truncated. The complementation of poxR401::Tn10 mutation suggests that poxR and the downstream ORF do not form an operon.

Example 2

Expression of poxR in a Bacteriophage T7 RNA Polymerase Expression System

The 2 kb DNA fragment capable of complementing the poxR mutation was cloned in both orientations under the control of bacteriophage T7 promoter in the vector pKSII (Stratagene, LaJolla, Calif.), to generate pMEG-251 and pMEG-273 (see FIG. 4). Expression and [$^{35}$S]-methionine labelling of plasmid-encoded polypeptides in a bacteriophage T7 expression system was carried out as described by Tabor and Richardson, *Proc. Natl. Acad. Sci. USA* 82:1074–1078 (1985) using *E. coli* BL21 (DE3) as host for the expression vectors (Studier and Moffat, *J. Mol. Biol.* 189:113–130 (1986)). Cell lysates of *E. coli* BL21 (DE3) carrying pMEG-251 showed a polypeptide with a molecular mass of about 35 kDa which was absent from lysates of cells carrying either pMEG-273 or the vector alone. The size of the expressed polypeptide is in complete agreement with the predicted size of poxR.

Example 3

Construction of poxR Defined Deletion Mutant Strains of *S. typhimudum*

A defined deletion of poxR was constructed by removing the 1018 bp BstB I-Xho I fragment of pMEG-273, filling in the termini with the large fragment of DNA polymerase I and religating, yielding plasmid pMEG-279. A 1 kb Xho I-Xba I fragment of pMEG-279, carrying the mutated ΔpoxR270 was subsequently recombined into the *S. typhimurium* UK-1 chromosome by bacterial mating according to the procedure described by Kaniga et al. (1994) with the following modification: 100 μl of fresh overnight culture of the donor *E. coli* strain MGN-617 (see Table 1) harboring the suicide plasmid pMEG-280 and 100 μl of the recipient *S. typhimurium* $_x$3761 were mixed in 5 ml of buffered saline gelatin (BSG). The solution was filtered through a 0.45 μm filter, which was then placed on the surface of an L-agar plate containing 100 μg/ml diaminopimelic acid (DAP), and incubated at 37° C. for at least 8 hours. Bacteria bound to the filter were then resuspended in 5 ml of BSG, and several dilutions were plated onto streptomycin selective plates. Single recombinants that had the plasmid integrated into the chromosome were grown in Luria broth (LB) in the absence of antibiotic selection, and several dilutions were plated on 5% sucrose to select for strains that had undergone resolution of the cointegrate by recombination. Double recombinants were tested for streptomycin sensitivity due to the lost of the suicide plasmid, for the poxR phenotype on AB2 plates, and for sensitivity to 1.25 mg/ml of protamine sulfate.

The deletion in poxR resulted in strain MGN-1036s (Table 1), where 270 amino acids of poxR have been deleted. MGN-1036s gave rise to microcolonies on AB2 medium as expected, consistent with the mutation being in the poxR gene. This was confirmed by Southern blot using the 2 kb DNA fragment encoding poxR as a probe. Moreover, the defined ΔpoxR270 was fully complemented by plasmid pMEG-274.

It has been reported that *S. typhimurium* mutants with reduced virulence also show sensitivity to antimicrobial cationic peptides such as defensin and protamine (Groissman et al., *Proc. Natl. Acad. Sci. USA* 89:11939–11943 (1992)). MGN-1036s failed to grow in presence of 1.25 mg/ml of protamine sulfate, while the isogenic wild-type exhibited normal growth at that concentration. This phenotype was complementable by pMEG-274. The defined deletion strain MGN-1036s was also found to be attenuated for virulence in mice. MGN-1036s was characterized biochemically using API strips. The results showed no biochemical difference between wild-type and poxR mutants. The growth rate of the defined deletion strain MGN-1036s was identical to that of the previous poxR mutants MGN-791s and MGN-816s. Taken together, the poxR defined mutant showed a phenotype identical to the transposon generated deletion strain and the insertion strain.

Example 4 poxR regulates the Expression of inv and sip Genes of Salmonella Pathogenicity Island I As described above, poxR mutations have attenuated virulence. Based on this, the possibility that poxR may regulate the expression of genes involved in S. typhimurium entry into eukaryotic cells was investigated. For this purpose, the effect of mutations in poxR on the expression of invF and sipC, two genes located in S. typhimurium pathogenicity island I and required for invasion of epithelial cells (Kaniga et al., Mol. Microbiol. 13(4):555–568 (1994); Kaniga et al. J. Bacteriol. 177(24):7078–7085 (1995)), was examined. Strains SB164 (Kaniga et al. (1994)) and SB227 (Kaniga et al. (1995)) carry chromosomal fusions of invF and sipC, respectively, to a xylE reporter gene. The poxR401::Tn10 mutation was introduced in SB164 and SB227 by P22 transduction to give SB164N and SB227N. Bacteriophage P22HTint was used for the transductions (Schmeiger (1972)).

To test whether the effect of poxR on invF and sipC expression was specific, a chromosomally integrated asd:.xylE fusion was constructed in poxR+ and poxR− genetic background to generate strain MGN-824s and MGN-1055s, respectively (see Table 1). To make the fusions, the 1.7 kb Bgl II fragment of cloning vector pYA292 (Galán et al., Gene 94(1):29–35 (1990)) which encodes the asd gene was subcloned into the Bam HI-Bgl II site of vector pIC20H (Marsh et al., Gene 32:481–485 (1984)) to generate pMEG-163. An internal 729 bp Eco RV fragment of the asd coding region was deleted and replaced by a 957 bp Bgl II promoterless xylE reporter from pSB383 (Kaniga et al. (1994)), generating pMEG-222. In pMEG-222, xylE expression is driven by the asd promoter. The Δasd729::xylE fusion was retrieved from pMEG-222 as a Bgl II-Xba I fragment which was then inserted into Bam HI-Xba I sites of the sucrose-based suicide vector pKNG101 (Kaniga et al., Gene 109:137–141 (1991)) to give pMEG-223. The Δasd729::xylE allele was introduced into the chromosome of S. typhimurium strain MGN-762s (poxR$^+$) and MGN-1036s (poxR−) by homologous recombination using the universal donor strain MGN-617 as described in Example 3, to produce MGN-824s and MGN-1055s, respectively.

The activity of catechol 2,3 dioxygenase in the different strains was measured as described previously (Kaniga et al. (1994)). The results are presented in FIG. 5. The results show that the poxR mutation specifically upregulates the expression of sipC and invF two- to three-fold, while the expression of asd gene was not affected.

It was then investigated whether the upregulation of invF and sipC genes was correlated with the secretion of the Sip proteins in the supernatant of Salmonella cultures. For this, proteins from cell-free culture supernatant were purified as described by Kaniga et al. (1995). Samples were separated by discontinuous sodium dodecyl sulfate (SDS)-polyacrylamide gel electrophoresis (PAGE). Gels were stained with brilliant blue R-250. Approximately 5-fold more Sip proteins were detected in the culture supernatant of a poxR[31] strain as compared to the isogenic wild-type. This phenotype was partially complementable by plasmid pMEG-274 carrying a cloned poxR gene. Interestingly, the amount of flagellin was identical in all strains, indicating that the effect of poxR mutation was Sips specific.

Example 5 poxR Gene is Present in other Pathogenic Microorganisms

Bacteria other than Salmonella, H. influenzae and E. coli were examined to determine if poxR was present in the genome of these bacterial species. Genomic DNA was purified from Shigella flexneri, Yersinia enterocolitica, Klebsiella pneumoniae, Pseudomonas aeruginosa, Pasteurella multocida, Borrellia burgdorferi, Mycobacterium tuberculosis and Erysipelothrix rhusiopathiae. 5 μg of genomic DNA were subjected to Southern blot analysis using a labelled 1 kb Bst BI-Xho I internal fragment of poxR as a probe (see FIG. 4). Despite the stringent hybridization and washing conditions (50° C.; 1×SSC; 0.1×SDS), a strong signal was detected in S. flexneri, Y. enterocolitica, K. pneumoniae and to a lesser extent, in P. multocida and M. tuberculosis. These data indicate that poxR is present in other organisms in addition to Salmonella, E. coli and H. influenzae.

Example 6 poxR Mutant Derivatives of S. typhimurium UK-1 are Avirulent in Day-old Chicks.

Day-old chicks are very sensitive to S. typhimurium UK-1 (Hassan and Curtiss, Infect. Immun. 62(12):5519–5527 (1994)). The 50% lethal dose (LD$_{50}$) of wild-type bacteria in day of hatch chicks in 3×10$^3$ cfu. Therefore, infant chicks are excellent models for S. typhimurium infection. It had been previously determined that the mean time to death of day-old chicks infected with 1×108 cfu of wild-type S. typhimurium UK-1 was 3 days. In order to determine whether the poxR mutation has any effect on virulence, five specific pathogen free white Leghorn chicken were inoculated by oral gavage with 1×10$^8$ cfu of strain MGN-791s (see Table 1) at day of hatch. Per oral inoculation (p.o.) of day-old chicks with S. typhimurium strains MGN-791s was performed according to Hassan and Curtiss. Under these conditions, all birds survived six days post-infection. To determine whether the survival of birds was due to the inability of the bacteria to disseminate in target organs, the colonization levels in the spleen, liver, bursa and cecum were determined six days post-infection (FIG. 1). The results show that the poxR mutant strain MGN 791s was able to colonize deep tissues. The survival of birds to 10,000 times the LD$_{50}$ dose is an indication of attenuation of virulence due to poxR mutation.

Example 7

Attenuation of Virulence and Colonization in Mice by poxR Mutants

To confirm the role of poxR mutation in virulence, the 50% lethal dose (LD$_{50}$) of S. typhimurium strain MGN-816s (see Table 1) was determined in mice. Treatment groups of six week-old female BALB/c mice were inoculated at day 1 either intra peritoneally (i.p.), or orally (p.o.) with the doses indicated in Table 2. Per oral inoculation (p.o.) and intraperitoneal (i.p.) inoculations of 6 week old female BALB/c mice with the different S. typhimurium strains were carried out as previously described (Galán and Curtiss (1989)). A non inoculated control group was included. Mice which survived immunization were challenged 35 days post-immunization by oral inoculation with 7.5×10$^8$ cfu of wild-type UK-1 strain $_x$3761. Control mice were challenged by oral inoculation with 1.5×10$^4$ cfu of wild type UK-1 strain $_x$3761 (the equivalent of LD$_{50}$). Three control mice died within 11 days post-challenge. The 2 remaining control mice were moribund and looked scruffy. They were euthanized and scored as dead from infection.

TABLE 2

| Route of immunization | Dose (cfu) of bacteria | Survivors following immunization | Survivors following challenge |
|---|---|---|---|
| Control | — | — | 0/5 |
| p.o. | 2.6 × 10$^7$ | 5/5 | 5/5 |
| p.o. | 2.6 × 10$^8$ | 5/5 | 5/5 |
| p.o. | 2.6 × 10$^9$ | 5/5$^a$ | 4/4$^b$ |
| i.p. | 2.6 × 10$^4$ | 5/5 | 5/5 |
| i.p. | 2.6 × 10$^5$ | 0/5 | — |

$^a$Eleven mice were immunized and three mice were euthanized on days 3 and 7 to determine the level of colonization in the spleen, mesenteric lymph nodes, and Peyer's patches.
$^b$One mouse in this group died during serum collection on day 28 post-infection.

Figure 2:
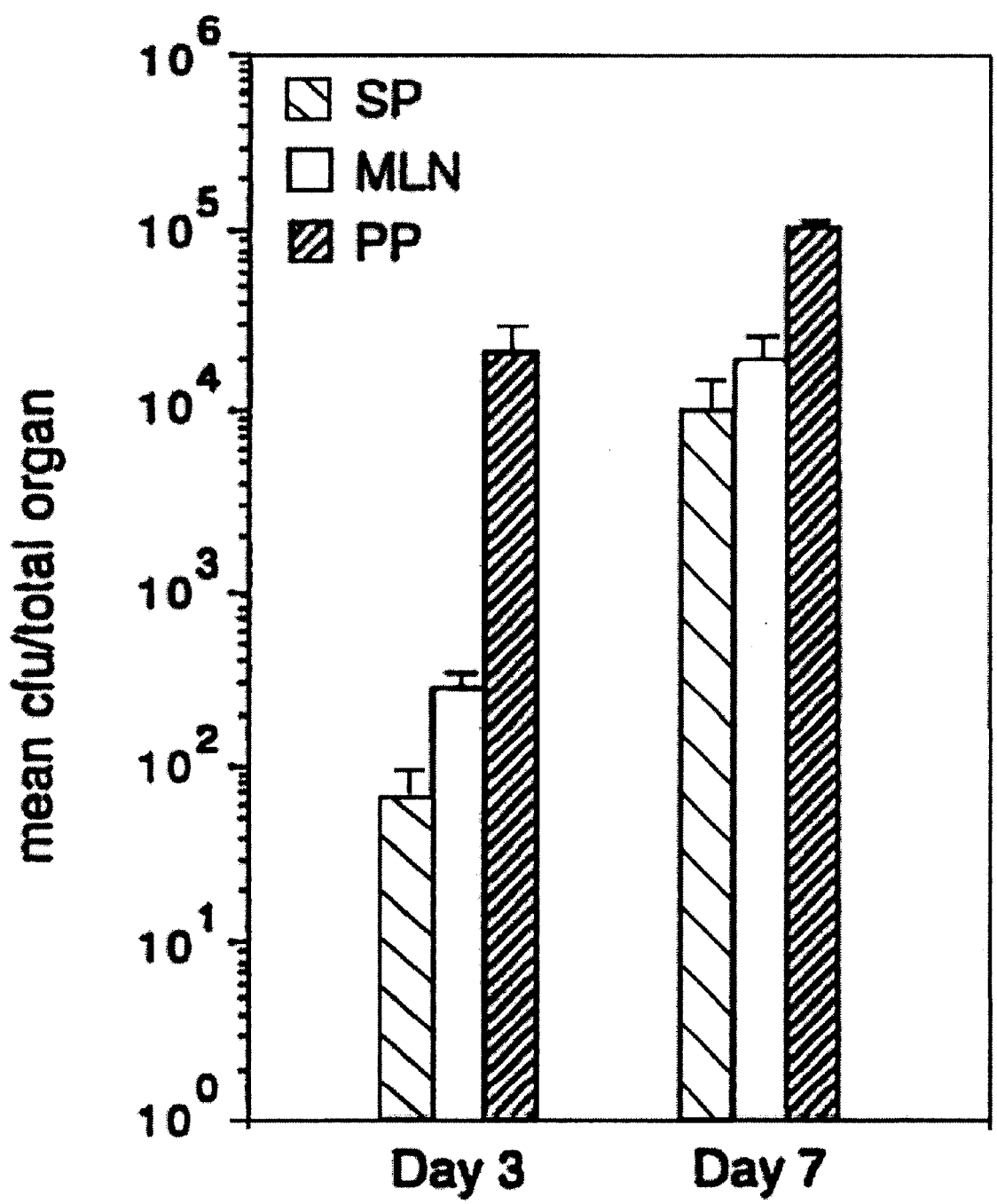

Three and seven days post-inoculation, three mice were humanely euthanized from the 2.6×10$^9$ cfu treatment group, and the colonization levels in the spleen, mesenteric lymph nodes and Peyer's patches were determined (FIG. 2). The results show greater than 10$^4$ cfu in both spleen and mesenteric lymph nodes, indicating that poxR mutant derivatives of S. typhimurium UK-1 are capable of colonizing deep tissues in mice following oral inoculation.

Following immunization, mice were monitored daily for death. All mice in the i.p. 2.6×10$^5$ cfu group died within 13 days post-infection. However, all mice from other treatment groups survived after 12 days post-inoculation (Table 2). The LD$_{50}$ of wild-type S. typhimurium UK-1 strain $_x$3761 was approximately 10 cfu for i.p., and 10$^4$ cfu for p.o. in six week-old female BALB/c mice. These results indicate that poxR mutants of S. typhimurium are avirulent in both i.p. and p.o. since mice inoculated with poxR mutant survived approximately 1,000 times the i.p. $LD_{50}$ of wild-type and 100,000 times the p.o. $LD_{50}$ of wild-type. The attenuation of virulence was not the result of the inability of the strain to colonize deep tissues (see above).

Example 8

Immunogenicity and Protection induced by *S. typhimurium* poxR Mutants

Six week old female BALB/c mice were immunized with single doses as indicated in Table 2. At day 28 post-immunization, sera were collected by retro orbital eye bleeding from immunized and non-immunized control mice. The humoral immune response of mice to *S. typhimurium* poxR mutant was measured by ELISA using purified LPS as coating antigen, since the O-antigen is the immunodominant antigen in Salmonella. The humoral response to *S. typhimurium* poxR mutants was assayed by either ELISA, or Western blot (immunoblot) of whole cell lysates proteins separated by SDS-PAGE, transferred to nitrocellulose, and detected using polyclonal antisera from immunized mice, followed by enhanced chemiluminescence (ECL kit; Amersham, Arlington Heights, Ill.). The results are shown in FIG. 3.

As expected, non-immunized control mice did not raise an immune response to Salmonella. However, mice immunized i.p. and p.o. raised strong IgA, IgM and IgG responses, indicating that poxR mutant derivatives of *S. typhimurium* induced a strong humoral immune response in mice. The humoral immune response measured in mice treated with $2.6\times10^9$ cfu p.o. appeared to be suppressed.

It was then determined whether the immune responses induced by *S. typhimurium* poxR mutants could protect mice against lethal wild-type challenge. Day 35 post-immunization, both i.p. and p.o. immunized mice were challenged by oral inoculation with $7.5\times10^8$ cfu of wild-type *S. typhimurium* UK-1 strain $_{x}$3761. The non-immunized control mice were challenged p.o. with $1.5\times10^4$ cfu of wild-type, the equivalent of $1.5\times LD_{50}$, to assess the virulence of the challenge strain. The experiment was terminated 16 days post-challenge and survivors following challenge were scored (Table 2). In the control treatment group, 5 of the 5 mice died by day 15 post-challenge. In immunized treatment groups, all mice survived approximately 10,000 times the $LD_{50}$ of wild-type challenge after a single immunization regimen. Taken together, these results demonstrate that poxR mutants are attenuated in mice and capable of inducing protective response against wild-type lethal challenge.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of inducing an immune response in an animal comprising administering a composition comprising bacterial cells and a pharmaceutically acceptable carrier to the animal, wherein the bacterial cells can colonize, infect, or grow in the animal and have a mutated poxA gene which attenuates the virulence of the cells, and wherein the composition is immunogenic.

2. The method of claim 1 wherein the bacterial cells express a heterologous gene.

3. The method of claim 1 wherein the bacterial cells contain a transfer vector.

4. The method of claim 3 wherein the transfer vector is one that can be transferred into a recipient cell and which contains a gene encoding a product selected from the group consisting of antigens, immunomodulators, enzymes, and expression products which regulate gene expression or cellular activity in the recipient cell.

5. The method of claim 4 wherein the recipient cell is an animal cell.

6. The method of claim 5 wherein the gene is operably linked to a promoter functional in the animal.

7. The method of claim 5 wherein the gene encodes β-galactosidase and is operably linked to an early intermediate cytomegalovirus promoter.

8. The method of claim 3 wherein the transfer vector includes an endA mutation or a recBC mutation.

9. The method of claim 2 wherein the heterologous gene encodes an antigen.

10. The method of claim 9 wherein the heterologous gene is operably linked to the promoter of any gene of the type III secretion system.

11. The method of claim 10 wherein the gene of the type III secretion system is selected from the group consisting of sip (ssp) genes, yop genes, ipa genes, and hrp genes.

12. The method of claim 9 wherein the antigen is expressed as a fusion to a Sip (Ssp), Yop, Ipa, or Hrp protein.

13. The method of claim 1 wherein the bacterial cells were produced from a bacterial cell in which a mutation in the poxA gene was produced by genetic manipulation.

14. The method of claim 1 wherein the mutated poxA gene is not expressed.

15. The method of claim 1 wherein the mutated poxA gene is not transcribed.

16. The method of claim 1 wherein the mutated poxA gene encodes a mutated PoxA protein.

17. The method of claim 1 wherein mRNA transcribed from the mutated poxA gene is not translated.

18. The method of claim 1 wherein the bacterial cells are in a family selected from the group consisting of Enterobacteriaceae, Micrococcaceae, Vibrionaceae, Pasteurellaceae, Mycoplasmataceae, and Rickettsiaceae.

19. The method of claim 18 wherein the bacterial cells are in a genus selected from the group consisting of Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, and Ehrlichia.

20. The method of claim 1 wherein the bacterial cells are in a genus selected from the group consisting of Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pedicoccus, Bacillus, Corynebacterium, Arcanobacterium, Actinomyces, Rhodococcus, Listeria, Erysipelothrix, Gardnerella, Neisseria, Camylobacter, Arcobacter, Wolinella, Heliobacter, Achomobacter, Acinetobacter, Agrobacterium, Alcaligenes, Chryseomonas, Comamonas, Eikenella, Flavimonas, Flavobacterium, Moraxella, Oligella, Pseudomonas, Skewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira, and Chlamydiae.

21. The method of claim 1 wherein the bacterial cells are selected from the group consisting of *Salmomella typhimurium, Escherichia coli, Haemophilus influenzae, Shigella flexneri, Yersinia enterocolitica, Klebsiella pneumoniae, Pasteurella multocida*, and *Mycobacterium tuberculosis.*

22. The method of claim 1 wherein the bacterial cells are *Salmonella typhimurium.*

* * * * *

```
                         SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 2007 base pairs
          (B) TYPE: nucleic acid
          (C) STRANDEDNESS: double
          (D) TOPOLOGY: linear (ii) MOLECULE TYPE: DNA (iii) HYPOTHETICAL: NO
```

-continued

```
    (iv) ANTI-SENSE: no (ix) FEATURE:
        (A) NAME/KEY: CDS
        (B) LOCATION: 345..1319
        (D) OTHER INFORMATION: /function= "encodes PoxR"

(ix) FEATURE:
        (A) NAME/KEY: CDS
        (B) LOCATION: 1548..2007

(xi) SEQUENCE DESCRIPTION: SEQ ID NO:1:

GATCGGCTTG AAAGGTTTGC ACGACATTCC TCCAGATTAT TGTAATTTCA CCCTCGCGCA      60

GCCAGATAAA GCCTCTGGGT TCTGCGAAGT ATGAATGCGT TTCCACTGCT CCTTTATGGG    120

TACAACAGTA TAGTCTCAGG GATGTGAGGG AAATTTGACG TGTTCGATTT TTTTAGCGTA    180

TCAGAGGGAT GAATTATCAT TGATTTTGAT TAATTTAATT ACTAAACCAT CTGAAATCAC    240

TTTTTTTACC CTCCAGAAGG CGCCCGATAC GCCTGCGCAA AATTTGTTTC GCCCGCGCGT    300

TGCGAGTAGA CTTCGTGACC TTGTCTTAAA CTGGAGAAAG AATC ATG AGC GAA ACG    356
                                                Met Ser Glu Thr
                                                  1

GCA ACC TGG CAG CCG AGC GCG TCC ATC CCC AAT TTA TTA AAA CGT GCG    404
Ala Thr Trp Gln Pro Ser Ala Ser Ile Pro Asn Leu Leu Lys Arg Ala
 5              10                  15                  20

GCG ATT ATG GCG GAA ATC CGT CGT TTC TTT GGC GAT CGT GGA GTG CTT    452
Ala Ile Met Ala Glu Ile Arg Arg Phe Phe Gly Asp Arg Gly Val Leu
              25                  30                  35

GAG GTT GAG ACG CCC TGC ATG AGT CAG GCG ACG GTC ACA GAC ATT CAT    500
Glu Val Glu Thr Pro Cys Met Ser Gln Ala Thr Val Thr Asp Ile His
         40                  45                  50

CTG TTC CCG TTC GAA ACG CGT TTC GTC GGA CCT GGC CAT TCC CAG GGG    548
Leu Phe Pro Phe Glu Thr Arg Phe Val Gly Pro Gly His Ser Gln Gly
     55                  60                  65

ATC AAC CTC TAT TTA ATG ACC AGT CCG GAA TAC CAT ATG AAA CGC CTG    596
Ile Asn Leu Tyr Leu Met Thr Ser Pro Glu Tyr His Met Lys Arg Leu
 70                  75                  80

CTG GAG GCA GGG TGC GGC CCG GTT TTC CAG CTA TGC CGC AGT TTC CGT    644
Leu Glu Ala Gly Cys Gly Pro Val Phe Gln Leu Cys Arg Ser Phe Arg
85                   90                  95                 100

AAT GAA GAG ATG GGA CGA CAT CAT AAT CCG GAA TTC ACT ATG CTG GAG    692
Asn Glu Glu Met Gly Arg His His Asn Pro Glu Phe Thr Met Leu Glu
                105                 110                 115

TGG TAT CGC CCG CAT TAC GAT ATG TAC CGC CTG ATG AAT GAA GTG GAT    740
Trp Tyr Arg Pro His Tyr Asp Met Tyr Arg Leu Met Asn Glu Val Asp
            120                 125                 130

GAT TTG CTT CAG CAA GTG CTG GAT TGT CAA CCT GCG GAA AGT CTC TCC    788
Asp Leu Leu Gln Gln Val Leu Asp Cys Gln Pro Ala Glu Ser Leu Ser
        135                 140                 145

TAT CAA CAG GCG TTT CAG CGC CAT CTG GGG ATT GAC CCG TTA TCA GCA    836
Tyr Gln Gln Ala Phe Gln Arg His Leu Gly Ile Asp Pro Leu Ser Ala
    150                 155                 160

GAT AAA ACG CAA CTG CGT GAG GCG GCG GCA AAG CTT GAT TTA AGC AAT    884
Asp Lys Thr Gln Leu Arg Glu Ala Ala Ala Lys Leu Asp Leu Ser Asn
165                 170                 175                 180

ATC GCC GAT ACG GAA GAA GAC CGT GAT ACG TTG CTG CAA CTG TTG TTC    932
Ile Ala Asp Thr Glu Glu Asp Arg Asp Thr Leu Leu Gln Leu Leu Phe
                185                 190                 195

ACG ATG GGG GTT GAG CCG CAT ATA GGT AAA GAA AAG CCG ACC TTT ATT    980
Thr Met Gly Val Glu Pro His Ile Gly Lys Glu Lys Pro Thr Phe Ile
            200                 205                 210
```

```
TAT CAC TTT CCG GCA AGT CAG GCA TCG CTG GCA CAA ATC AGT ACC GAG       1028
Tyr His Phe Pro Ala Ser Gln Ala Ser Leu Ala Gln Ile Ser Thr Glu
        215                 220                 225

GAT CAT CGC GTC GCC GAG CGC TTT GAG GTG TAC TAC AAA GGT ATT GAG       1076
Asp His Arg Val Ala Glu Arg Phe Glu Val Tyr Tyr Lys Gly Ile Glu
        230                 235                 240

CTG GCG AAT GGT TTC CAC GAA CTG ACG GAC GCA CGT GAG CAA CAA CAG       1124
Leu Ala Asn Gly Phe His Glu Leu Thr Asp Ala Arg Glu Gln Gln Gln
245                 250                 255                 260

CGC TTT GAA CAG GAC AAT CGT AAG CGC GCC GCT CGC GGT CTG GCG CAG       1172
Arg Phe Glu Gln Asp Asn Arg Lys Arg Ala Ala Arg Gly Leu Ala Gln
                265                 270                 275

CAG CCG ATG GAC CAA AAT CTA CTG GAT GCG CTG GCC GCC GGT CTA CCG       1220
Gln Pro Met Asp Gln Asn Leu Leu Asp Ala Leu Ala Ala Gly Leu Pro
                280                 285                 290

GAT TGT TCC GGC GTG GCG CTG GGT GTT GAT CGT CTG GTG ATG CTG GCG       1268
Asp Cys Ser Gly Val Ala Leu Gly Val Asp Arg Leu Val Met Leu Ala
                295                 300                 305

CTG GGA GCA GAA AGC CTG GCG GAC GTG ATT GCT TTT ACG GTC GAT CGG       1316
Leu Gly Ala Glu Ser Leu Ala Asp Val Ile Ala Phe Thr Val Asp Arg
        310                 315                 320

GCG TAA ATCTGAAATT CACTCTTTCG CGAGAGAAAA TGGCGCAATA AGCGCCATTT        1372
Ala
325

TGTAGCATAT TTTTTCAATT ATCCTCTGTT TGGCACAACA TAAGGCTGGA ACTTTGATGC     1432

CATTTAGGTA TCAATCCTGT GTTGATTTTT TTATCGCTGA CCTTCGTAAA AAGAAGGCG     1492

GCGTCAATCG GTGAGCGGCG TCTGGCAAAC GCGCTCGAGC GTAAGGGATG GTTGA ATG     1550
                                                             Met
                                                             1

ACC CAC ACG ATA AAA AAG ATG AGC CTT ATT GGG CTT ATC CTG ATG ATT      1598
Thr His Thr Ile Lys Lys Met Ser Leu Ile Gly Leu Ile Leu Met Ile
            5                   10                  15

TTT ACT TCT GTT TTT GGT TTT GCG AAT AGC CCG TCG GCG TTT TAT TTA      1646
Phe Thr Ser Val Phe Gly Phe Ala Asn Ser Pro Ser Ala Phe Tyr Leu
        20                  25                  30

ATG GGG TAT AGC GCA ATC CCA TGG TAT ATA TTT TCT GCC TTG CTG TTT      1694
Met Gly Tyr Ser Ala Ile Pro Trp Tyr Ile Phe Ser Ala Leu Leu Phe
        35                  40                  45

TTT ATT CCA TTC GCC TTA ATG ATG GCT GAA ATG GGT TCC GCT TAT CCC      1742
Phe Ile Pro Phe Ala Leu Met Met Ala Glu Met Gly Ser Ala Tyr Pro
50                  55                  60                  65

AAA GAA GAG GGC GGG ATC TAT TCG TGG ATG AAT AAT AGC GTG GGG CCA      1790
Lys Glu Glu Gly Gly Ile Tyr Ser Trp Met Asn Asn Ser Val Gly Pro
            70                  75                  80

CGT TAC GCG TTT ATT GGC ACG TTT ATG TGG TTT TCA TCG TAT GTC ATA      1838
Arg Tyr Ala Phe Ile Gly Thr Phe Met Trp Phe Ser Ser Tyr Val Ile
        85                  90                  95

TGG ATG GTA AGT ACG GCG GCA AAA ATT TGG GTA CCG TTT TCT ACA TTT      1886
Trp Met Val Ser Thr Ala Ala Lys Ile Trp Val Pro Phe Ser Thr Phe
        100                 105                 110

GTT TTT GGC CCC GAT ATG ACG CAG CAC TGG CGT ATT GCA GGG CTT GAG      1934
Val Phe Gly Pro Asp Met Thr Gln His Trp Arg Ile Ala Gly Leu Glu
        115                 120                 125

CCT ACG CAG GTT GTC GGG CTG CTC GCC GTC GGC TGG ATG AAT CTG GTG      1982
Pro Thr Gln Val Val Gly Leu Leu Ala Val Gly Trp Met Asn Leu Val
130                 135                 140                 145

ACG TGT GTC GCC GCC AGA GGG ATC C                                    2007
Thr Cys Val Ala Ala Arg Gly Ile
```

150

(2) INFORMATION FOR SEQ ID NO:2:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Glu Thr Ala Thr Trp Gln Pro Ser Ala Ser Ile Pro Asn Leu
 1               5                  10                  15

Leu Lys Arg Ala Ala Ile Met Ala Glu Ile Arg Arg Phe Phe Gly Asp
            20                  25                  30

Arg Gly Val Leu Glu Val Glu Thr Pro Cys Met Ser Gln Ala Thr Val
        35                  40                  45

Thr Asp Ile His Leu Phe Pro Phe Glu Thr Arg Phe Val Gly Pro Gly
    50                  55                  60

His Ser Gln Gly Ile Asn Leu Tyr Leu Met Thr Ser Pro Glu Tyr His
65                  70                  75                  80

Met Lys Arg Leu Leu Glu Ala Gly Cys Gly Pro Val Phe Gln Leu Cys
                85                  90                  95

Arg Ser Phe Arg Asn Glu Glu Met Gly Arg His His Asn Pro Glu Phe
            100                 105                 110

Thr Met Leu Glu Trp Tyr Arg Pro His Tyr Asp Met Tyr Arg Leu Met
        115                 120                 125

Asn Glu Val Asp Asp Leu Leu Gln Gln Val Leu Asp Cys Gln Pro Ala
    130                 135                 140

Glu Ser Leu Ser Tyr Gln Gln Ala Phe Gln Arg His Leu Gly Ile Asp
145                 150                 155                 160

Pro Leu Ser Ala Asp Lys Thr Gln Leu Arg Glu Ala Ala Lys Leu
                165                 170                 175

Asp Leu Ser Asn Ile Ala Asp Thr Glu Glu Asp Arg Asp Thr Leu Leu
            180                 185                 190

Gln Leu Leu Phe Thr Met Gly Val Glu Pro His Ile Gly Lys Glu Lys
        195                 200                 205

Pro Thr Phe Ile Tyr His Phe Pro Ala Ser Gln Ala Ser Leu Ala Gln
    210                 215                 220

Ile Ser Thr Glu Asp His Arg Val Ala Glu Arg Phe Glu Val Tyr Tyr
225                 230                 235                 240

Lys Gly Ile Glu Leu Ala Asn Gly Phe His Glu Leu Thr Asp Ala Arg
                245                 250                 255

Glu Gln Gln Gln Arg Phe Glu Gln Asp Asn Arg Lys Arg Ala Ala Arg
            260                 265                 270

Gly Leu Ala Gln Gln Pro Met Asp Gln Asn Leu Leu Asp Ala Leu Ala
        275                 280                 285

Ala Gly Leu Pro Asp Cys Ser Gly Val Ala Leu Gly Val Asp Arg Leu
    290                 295                 300

Val Met Leu Ala Leu Gly Ala Glu Ser Leu Ala Asp Val Ile Ala Phe
305                 310                 315                 320

Thr Val Asp Arg Ala
            325
```

(2) INFORMATION FOR SEQ ID NO:3:

```
    (i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:3:

Met Thr His Thr Ile Lys Lys Met Ser Leu Ile Gly Leu Ile Leu Met
1               5                   10                  15

Ile Phe Thr Ser Val Phe Gly Phe Ala Asn Ser Pro Ser Ala Phe Tyr
            20                  25                  30

Leu Met Gly Tyr Ser Ala Ile Pro Trp Tyr Ile Phe Ser Ala Leu Leu
            35                  40                  45

Phe Phe Ile Pro Phe Ala Leu Met Met Ala Glu Met Gly Ser Ala Tyr
        50                  55                  60

Pro Lys Glu Glu Gly Gly Ile Tyr Ser Trp Met Asn Asn Ser Val Gly
65                  70                  75                  80

Pro Arg Tyr Ala Phe Ile Gly Thr Phe Met Trp Phe Ser Ser Tyr Val
                85                  90                  95

Ile Trp Met Val Ser Thr Ala Ala Lys Ile Trp Val Pro Phe Ser Thr
                100                 105                 110

Phe Val Phe Gly Pro Asp Met Thr Gln His Trp Arg Ile Ala Gly Leu
            115                 120                 125

Glu Pro Thr Gln Val Val Gly Leu Leu Ala Val Gly Trp Met Asn Leu
        130                 135                 140

Val Thr Cys Val Ala Ala Arg Gly Ile
145                 150
```